(12) United States Patent
Aikawa

(10) Patent No.: US 9,404,184 B2
(45) Date of Patent: Aug. 2, 2016

(54) SUBSTRATE POSITION DETECTING APPARATUS, SUBSTRATE PROCESSING APPARATUS USING SUBSTRATE POSITION DETECTING APPARATUS, AND DEPOSITION APPARATUS

(71) Applicant: Tokyo Electron Limited, Tokyo (JP)

(72) Inventor: Katsuyoshi Aikawa, Iwate (JP)

(73) Assignee: Tokyo Electron Limited, Tokyo (JP)

( * ) Notice: Subject to any disclaimer, the term of this patent is extended or adjusted under 35 U.S.C. 154(b) by 314 days.

(21) Appl. No.: 14/104,049

(22) Filed: Dec. 12, 2013

(65) Prior Publication Data

US 2014/0174351 A1 Jun. 26, 2014

(30) Foreign Application Priority Data

Dec. 21, 2012 (JP) ................................. 2012-279911

(51) Int. Cl.
| | |
|---|---|
| *C23C 16/52* | (2006.01) |
| *C23C 16/44* | (2006.01) |
| *C23C 16/455* | (2006.01) |
| *H01L 21/67* | (2006.01) |
| *H01L 21/68* | (2006.01) |
| *H01L 21/687* | (2006.01) |
| *G01N 21/15* | (2006.01) |
| *G01N 21/95* | (2006.01) |

(52) U.S. Cl.
CPC ................. *C23C 16/52* (2013.01); *C23C 16/44* (2013.01); *C23C 16/45551* (2013.01); *H01L 21/67259* (2013.01); *H01L 21/681* (2013.01); *H01L 21/68764* (2013.01); *H01L 21/68771* (2013.01); *G01N 21/15* (2013.01); *G01N 21/9501* (2013.01)

(58) Field of Classification Search
None
See application file for complete search history.

(56) References Cited

U.S. PATENT DOCUMENTS

| | | | | |
|---|---|---|---|---|
| 2003/0219914 A1* | 11/2003 | Gaudon | ............. | G06K 7/10861 438/14 |
| 2008/0192113 A1* | 8/2008 | Kilian | ................... | B60T 17/228 348/61 |
| 2010/0055312 A1* | 3/2010 | Kato | ................. | C23C 16/45502 427/255.26 |
| 2010/0124610 A1* | 5/2010 | Aikawa | ............... | C23C 16/4584 427/255.28 |
| 2012/0183676 A1* | 7/2012 | Sonoda | ................. | C23C 14/042 427/8 |

FOREIGN PATENT DOCUMENTS

| | | |
|---|---|---|
| JP | H05-125548 | 5/1993 |
| JP | 2002-162258 | 6/2002 |
| JP | 2010-153769 | 7/2010 |
| JP | 2012-094814 | 5/2012 |

* cited by examiner

*Primary Examiner* — Charles Capozzi
(74) *Attorney, Agent, or Firm* — IPUSA, PLLC

(57) ABSTRACT

A substrate position detecting apparatus detects a position of a substrate inside a chamber from an image of a target inside the chamber. The apparatus includes an image pickup device to pick up the image of the target inside the chamber through a window, an illumination device to irradiate light upwards, an illumination reflecting plate provided above the illumination device and including a reflecting surface to reflect the light from the illumination device towards the window, and a reflection restricting part provided on the reflecting surface to form a shadow in a predetermined region that includes the target inside the chamber.

18 Claims, 17 Drawing Sheets

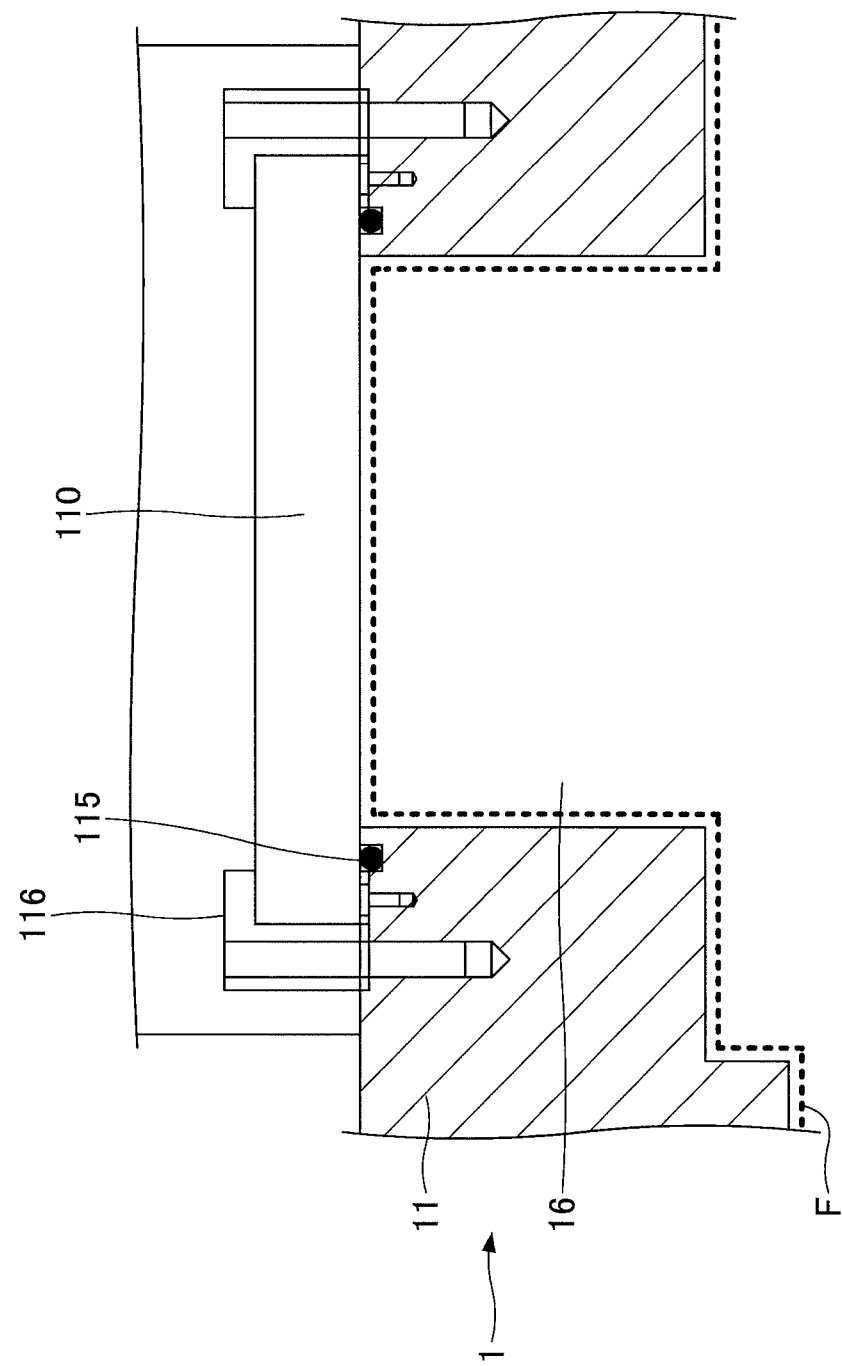

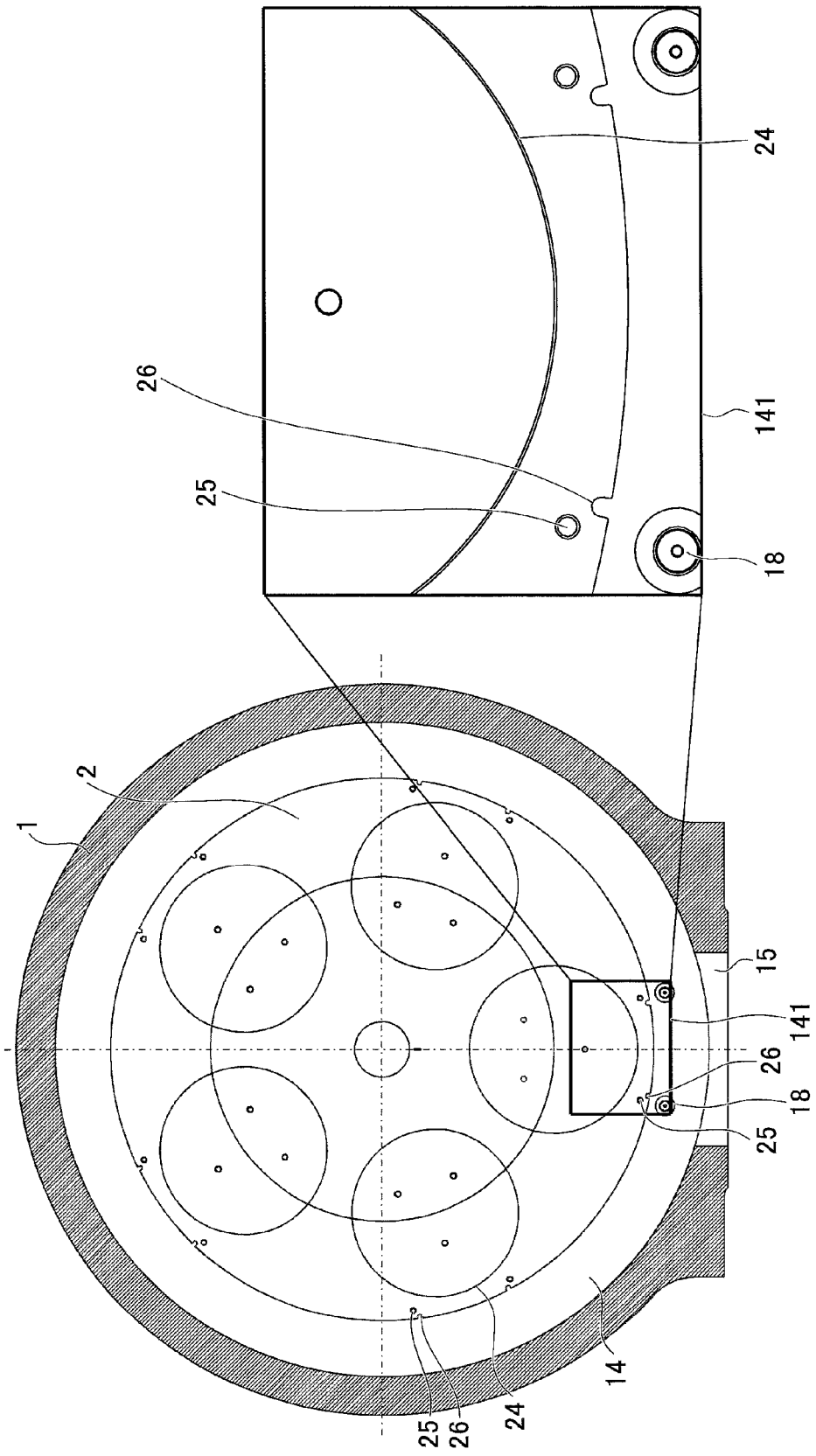

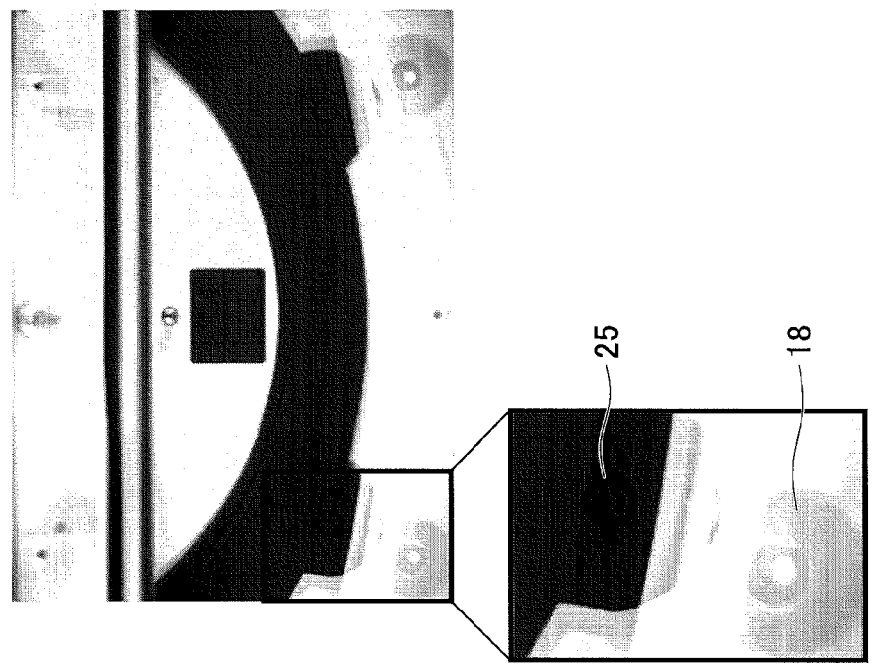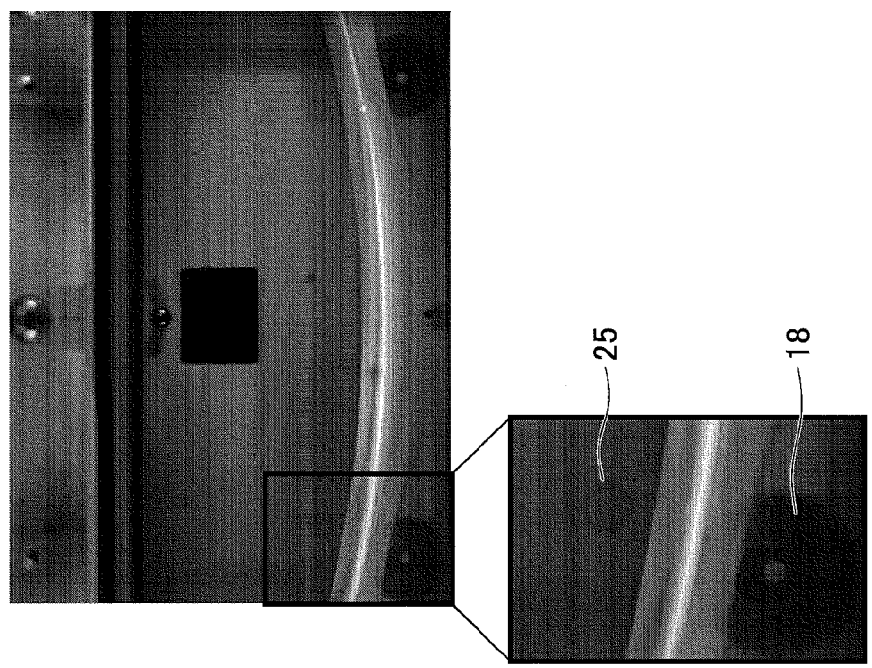

SUBSTRATE POSITION DETECTING APPARATUS, SUBSTRATE PROCESSING APPARATUS USING SUBSTRATE POSITION DETECTING APPARATUS, AND DEPOSITION APPARATUS

CROSS-REFERENCE TO RELATED APPLICATIONS

This application is based upon and claims the benefit of priority of Japanese Patent Application No. 2012-279911, filed on Dec. 21, 2012, the entire contents of which are incorporated herein by reference.

BACKGROUND OF THE INVENTION

1. Field of the Invention

The present invention relates to a substrate position detecting apparatus, a substrate processing apparatus using the substrate position detecting apparatus, and a deposition apparatus.

2. Description of the Related Art

A known substrate position detecting apparatus may include an image pickup device to pick up an image of a substrate that is a target of position detection, a light scattering panel member arranged between the image pickup device and the substrate and having a first opening to secure a field of view of the image pickup device with respect to the substrate, a first illumination device to illuminate the panel member with light, and a processing unit to obtain a position of the substrate from the image of the substrate picked up by the image pickup device (for example, Japanese Laid-Open Patent Publication No. 2010-153769).

The substrate position detecting apparatus proposed in Japanese Laid-Open Patent Publication No. 2010-153769 is arranged above a window that is formed at a top surface of a chamber of a deposition apparatus, and detects the position of a wafer (substrate) within the chamber via the window. In the substrate position detecting apparatus proposed in Japanese Laid-Open Patent Publication No. 2010-153769, the panel member is formed by an acrylic plate coated with white pigments, and light is irradiated on the panel member so that the panel member makes white emission, in order to make the wafer appear white. On the other hand, a susceptor on which the wafer is placed may be made of carbon or SiC coated carbon, and such a susceptor appears black when illuminated by the light from the panel member. Contrast between the white-appearing wafer and the black-appearing susceptor enables clear recognition of a wafer edge, in order to reduce detection error.

However, according to the substrate position detecting apparatus proposed in Japanese Laid-Open Patent Publication No. 2010-153769, deposition may occur on an inner side of the window provided on the chamber as the deposition within the chamber progresses. In a case in which the deposition causes a colored film having reflectivity to be formed on the window, the film may reflect light at the window to thereby deteriorate the contrast of the image picked up by the image pickup device.

SUMMARY OF THE INVENTION

Accordingly, embodiments of the present invention may provide a substrate position detecting apparatus, a substrate processing apparatus using the substrate position detecting apparatus, and a deposition apparatus, that may pick up an image of an image pickup target within a chamber with a high contrast in order to detect a position of a substrate.

According to one aspect of the present invention, a substrate position detecting apparatus that detects a position of a substrate inside a chamber from an image of a target inside the chamber, may include an image pickup device provided above a window that is provided on a top surface of the chamber and configured to pick up the image of the target inside the chamber through the window; an illumination device provided above the window and configured to irradiate light upwards; an illumination reflecting plate provided above the illumination device and including a reflecting surface configured to reflect the light from the illumination device towards the window; and a reflection restricting part provided on the reflecting surface of the illumination reflecting plate and configured to form a shadow in a predetermined region that includes the target inside the chamber.

According to another aspect of the present invention, a substrate processing apparatus may include a chamber including a top surface provided with a window, configured to process a substrate inside the chamber; a susceptor on which the substrate is set, provided inside the chamber; and the substrate position detecting apparatus described above, wherein the susceptor further includes a third mark formed by a cutout in a part of the susceptor, located in a vicinity of the second mark.

According to still another aspect of the present invention, a deposition apparatus may include a chamber including a top surface provided with a window, configured to process a substrate inside the chamber; a susceptor on which the substrate is set, provided inside the chamber; the substrate position detecting apparatus described above; a first processing region provided inside the chamber and configured to receive a first reaction gas supplied thereto; a second processing region provided inside the chamber, separated from the first processing region, and configured to receive a second reaction gas supplied thereto; and a separation region provided between the first and second processing regions and having a ceiling surface lower than those of the first and second processing regions, and configured to receive a separation gas supplied thereto in order to suppress mixing of the first and second reaction gases.

According to another aspect of the present invention, a deposition apparatus may include a substrate processing apparatus described above; a first processing region provided inside the chamber of the substrate processing apparatus and configured to receive a first reaction gas supplied thereto; a second processing region provided inside the chamber, separated from the first processing region, and configured to receive a second reaction gas supplied thereto; and a separation region provided between the first and second processing regions and having a ceiling surface lower than those of the first and second processing regions, and configured to receive a separation gas supplied thereto in order to suppress mixing of the first and second reaction gases.

BRIEF DESCRIPTION OF THE DRAWINGS

FIG. 3 is an enlarged view illustrating a relationship between a window in the substrate processing apparatus that includes the substrate position detecting apparatus in the first embodiment of the present invention and a hole in the chamber;

FIGS. 6A and 6B are diagrams illustrating a layout relationship of each of the marks within the chamber in the example of the substrate processing apparatus in the first embodiment;

FIGS. 7A and 7B are diagrams illustrating an image of the marks picked up by a conventional substrate position detecting apparatus in comparison with an image picked up by the substrate position detecting apparatus in the first embodiment;

DESCRIPTION OF THE PREFERRED EMBODIMENTS

A description will hereinafter be given of embodiments of the present invention with reference to the drawings.

First Embodiment

Figure 1:
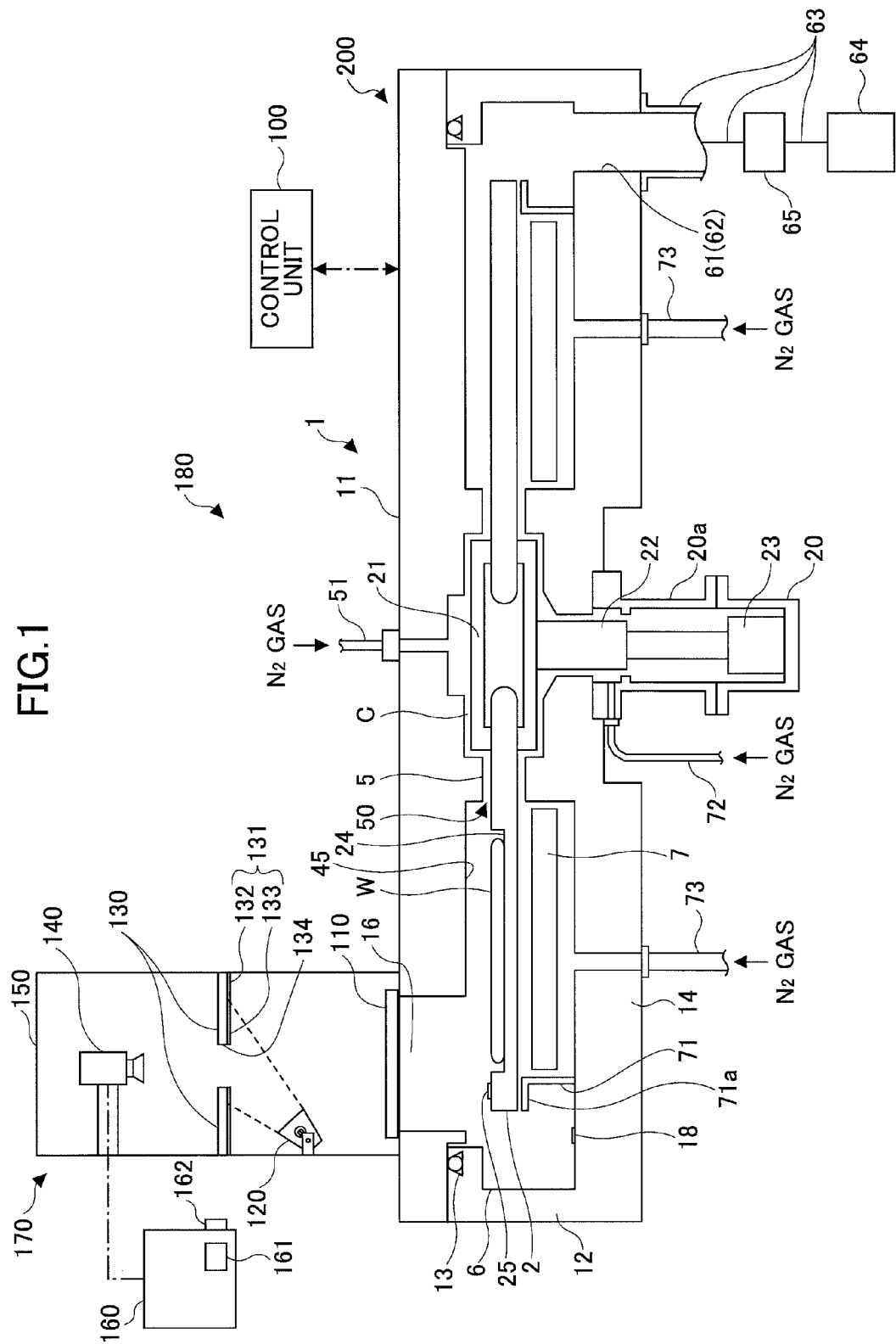
FIG. 1 is a diagram illustrating an example of a substrate processing apparatus that includes a substrate position detecting apparatus in a first embodiment of the present invention.

FIG. 1 is a diagram illustrating an example of a substrate processing apparatus that includes a substrate position detecting apparatus in a first embodiment of the present invention. In FIG. 1, a substrate position detecting apparatus 170 in the first embodiment may include an illumination 120 that is an example of an illumination means or an illumination device, an illumination reflecting plate 130, a camera 140, a housing 150, and a processing part 160. A substrate processing apparatus 180 may include, in addition to the substrate position detecting apparatus 170, a chamber 1, a susceptor 2, a window 110, and a rotational shaft 22. The substrate processing apparatus 180 may also include various constituent elements within the chamber 1, and various constituent elements mounted on the chamber 1, that are required for the processing of a substrate, if necessary. FIG. 1 also illustrates a wafer W that is an example of the substrate that is a position detecting target.

The chamber 1 is an example of a process container for processing the substrate, such as the wafer W. The chamber 1 to which the substrate position detecting apparatus 170 in the first embodiment is applied may be any chamber for processing the substrate, wherein the window 110 may reflect light, and contents of the substrate processing within the chamber 1 may be arbitrary. Accordingly, the substrate processing apparatus 170 may be formed to perform various substrate processing. However, in the first embodiment, it is assumed for the sake of convenience that the chamber 1 is an example of a deposition chamber in which a deposition process is performed.

As illustrated in FIG. 1, the chamber 1 may include a top plate 11 and a container body 12, and form a closed or sealed container as a whole. In the substrate processing apparatus 180 in this first embodiment, a hole 16 is provided in a part of the top plate 11 in order to enable the camera 140 to pick up an inside of the chamber 1. The hole 16 is an example of an opening that communicates to the inside of the chamber 1, and the window 110 may be arranged to cover the hole 16 in order to seal the chamber 1.

Figure 2:
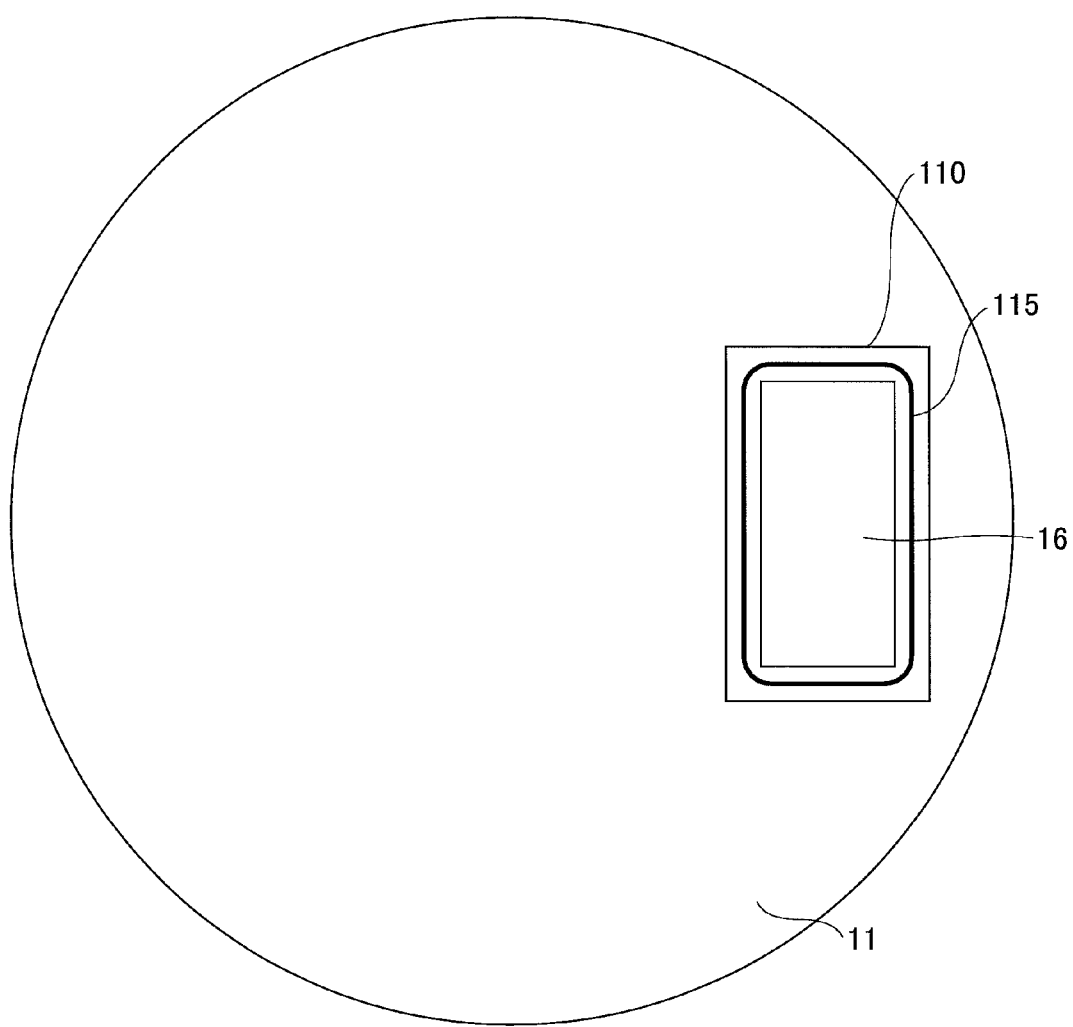
FIG. 2 is a diagram illustrating a top surface of a chamber in the example of the substrate processing apparatus that includes the substrate position detecting apparatus in the first embodiment of the present invention.

FIG. 2 is a diagram illustrating a top surface of the chamber in the example of the substrate processing apparatus that includes the substrate position detecting apparatus in the first embodiment of the present invention. As illustrated in FIG. 2, the top surface of the chamber 1 may be formed by the top plate 11, and the hole 16 may be formed in a part of the top plate 11. The window 110 is slightly larger than the hole 16, and is provided to cover the hole 16. The hole 16 is sealed by the top plate 11 via an O-ring 115.

Returning now to the description of FIG. 1, generally, when the deposition process is to be performed using the chamber 1, the inside of the chamber 1 may be set to a high temperature, and a reaction gas for the deposition may be supplied inside the chamber 1. The substrate processing apparatus 180 in the first embodiment may perform a deposition process using an ALD (Atomic Layer Deposition) to form an atomic layer on the wafer W, or using an MLD (Molecular Layer Deposition) to form a molecular layer on the wafer W, as will be described by referring to examples.

The chamber 1 may include a chamber mark 18. The chamber mark 18 may indicate a reference position of the chamber 1, and the position of the wafer W may be detected with reference to the chamber mark 18. Details of the chamber mark 18 will be described later in the specification.

The susceptor 2 is an example of a substrate setting base on which the wafer W is set, and the susceptor 2 may be provided inside the chamber 1. A surface of the susceptor 2 may include a plurality of recesses 24 respectively having a size approximately the same as that of the wafer W and a concave shape forming a substrate setting region in which the wafer W is set. The recess (hereinafter also referred to as "substrate setting region") 24 may be formed so that the wafer W is set at a predetermined position. In addition, the susceptor 2 may be formed to a circular disk shape, and a plurality of wafers W may be set along a circumferential direction of the susceptor 2. The susceptor 2 may be connected to the rotational shaft 22 and rotatably supported. The susceptor 2 may also be referred to as a "rotary table 2".

Because the susceptor 2 is rotatable, the position of the wafer W set on the susceptor 2 is not fixed, and the position of the wafer W needs to be detected when performing the deposition process. As described above, the wafer W may be set in the recess 24 of the susceptor 2, and thus, a colored susceptor mark 25 may be provided on the surface of the susceptor 2. The position of the wafer W may be detected by detecting the colored susceptor mark 25. Details of the susceptor mark 25 will be described later in the specification.

In this example, since the susceptor 2 has the circular shape, the chamber 1 that accommodates the susceptor 1 may have a corresponding cylindrical shape.

The window 110 may be provided over the hole 16 in order to seal the opening formed by the hole 16, and secure a field of view of the camera 140 that is provided above the window 110 with respect to the wafer W. The window 110 may be formed by any one of various materials that transmits light, and the window 110 may be formed by quartz glass, for example.

FIG. 3 is an enlarged view illustrating a relationship between the window in the substrate processing apparatus that includes the substrate position detecting apparatus in the first embodiment of the present invention and the hole in the chamber. As illustrated in FIG. 3, the window 110 may be arranged over the hole 16 formed in the top plate 11 forming the top surface of the chamber 1. The O-ring 115 may be provided between the window 110 and the top plate 11. A window fastener 116 may be screwed into the top plate 11 in order to hold the window 110 from the top surface and side surfaces thereof, and fix the window 110 to cover and seal the hole 16. Because the window 110 is provided to cover and seal the hole 16 provided in the top surface of the chamber 1, the seal of the chamber 1 may be maintained, and in addition, the inside of the chamber 1 may be monitored through the window 110.

Because the window 110 is configured to substantially form the top surface of the chamber 1, deposition may occur on an inner surface of the window 110 as the deposition process progresses. A dotted line F in FIG. 3 schematically illustrates a film deposited on the inner surface of the window 110. Basically, a source gas for the deposition is supplied to the wafer W on the susceptor 2, and the deposition occurs on the wafer W. For this reason, the film deposited on the inner surface of the window 110 may be on the order of $\frac{1}{10}$ the thickness of the film deposited on the wafer W. In the substrate processing apparatus using the ALD or MLD, the deposition on the wafer W on the atomic layer level or the molecular layer level, and this is the reason why the film deposited on the inner surface of the window 110 that is not the deposition target is relatively thin. This is a difference compared to a CVD (Chemical Vapor Deposition) reaction in which a relatively thick film would be formed not only on the surface of the wafer W but also on the inner surface of the window W. The film deposited on the inner surface of the window 110 in the substrate processing apparatus using the ALD or the MLD may thus be periodically cleaned using a cleaning gas, so as not to affect detection of the colored susceptor mark 25.

However, when a reflective film, such as a TiN film, is formed on the inner surface of the window 110, visibility of the colored susceptor mark 25 may deteriorate between periodic cleaning using the cleaning gas. The first embodiment may provide a substrate position detecting apparatus and a substrate processing apparatus that may positively detect the colored susceptor mark 25, even in a case in which the reflective film is deposited on the inner surface of the window 110.

Returning now to the description of FIG. 1, the illumination 120 may be formed by a light source that irradiates light upwards therefrom towards the illumination reflecting plate 130, so that reflected light from the illumination reflecting plate 130 may become incident to the window 110. The illumination 120 may be formed by various light sources capable of irradiating the illumination reflecting plate 130 with a suitable luminance. For example, an LED (Light Emitting Diode) may be used as the light source. The illumination 120 may be provided in a vicinity of a wall surface of the housing 150, in order not to block the field of view of the image pickup, and irradiate light in an oblique upward direction.

The illumination reflecting plate 130 is an example of a light reflecting means or a light reflecting part that reflects the light incident thereto from the illumination 120, irradiates the window 110 with the reflected light, and illuminates the inside of the chamber 1. The illumination reflecting plate 130 may include a reflecting surface 131 on a lower surface thereof in order to reflect the light incident thereto from under the illumination reflecting plate 130. The illumination reflecting plate 130 of the substrate position detecting apparatus 170 in the first embodiment may include, on the reflecting surface 131, not only a part reflecting the light, but also a reflection restricting part that forms a shadow in a predetermined region within the field of view of the image pickup of the camera 140, as will be described later in the specification.

The illumination reflecting plate 130 may include an opening 134 so as not to block the field of view of the camera 140. In FIG. 1, the opening 134 is required because the illumination reflecting plate 130 is provided under the camera 140, however, the illumination reflecting plate 130 may be provided above the camera 140. In this case, the opening 134 in the illumination reflecting plate 130 may be omitted, and the illumination reflecting plate 130 may be formed to a single continuous plate shape.

The camera 140 forms an example of an image pickup means or an image pickup device that picks up the image inside the chamber 1 via the window 110. Various camera configurations may be used for the camera 140 to suit the purpose, and for example, a CCD (Charge Coupled Device) may be used for the camera 140.

The housing 150 may accommodate the window 110, the illumination 120, the illumination reflecting plate 130, and the camera 140. By covering the window 110, the illumination 120, the illumination reflecting plate 130, and the camera 140 in their entirety, the housing 150 may make a surrounding of the camera dark and provide a state suited for the image pickup by the camera 140.

The processing part 160 is an example of a processing means or a processing unit that performs a computing process to detect the position of the substrate, that is, the wafer W, based on the image picked up by the camera 140. The processing part 160 may include a CPU (Central Processing Unit) and be configured to perform the computing process. The processing part 160 may also be formed by a microcomputer that operates by executing a program, or an integrated circuit such as an ASIC (Application Specific Integrated Circuit) or the like that is designed and fabricated for a specific purpose.

The processing part 160 may include a susceptor mark selection judging part 161 if necessary. The susceptor mark selection judging part 161 may perform a judging process in order to select an appropriate susceptor mark according to a deposition state, in a case in which a plurality of kinds of susceptor marks exist. For example, the susceptor mark judging part 161 may judge whether to use the colored susceptor mark 25 or the cutout susceptor mark 26, according to visibility of the cutout susceptor mark 26. The judging process may also be a computing process, and thus, the susceptor mark selection judging part 161 may be provided within the processing part 160. However, the susceptor mark selection judging part 161 does not necessarily have to be provided within the processing part 160. In other words, the susceptor mark selection judging part 161 may be provided independently (or separately) from the processing part 160, and be coupled externally to the processing part 160, to suit the purpose.

The processing part 160 may include a susceptor mark selection switch 162 if necessary. The selection of the susceptor mark may be judged by a user, and the susceptor mark selection switch 162 may be provided to enable the user to use a desired susceptor mark for the substrate position detection. At least one of the susceptor mark selection judging part 161 and the susceptor mark selection switch 162 may be provided, but it is of course possible to provide both the susceptor mark selection judging part 161 and the susceptor mark selection switch 162. Both the susceptor mark selection judging part 161 and the susceptor mark selection switch 162 may be provided, by normally following the judgment of the susceptor mark selection judging part 161, and placing priority on a selection operation of the susceptor mark selection switch 162 in a case in which the susceptor mark selection switch 162 is operated.

Various other constituent elements of the substrate processing apparatus 180 illustrated in FIG. 1 will be given later in the specification.

Figure 4A:
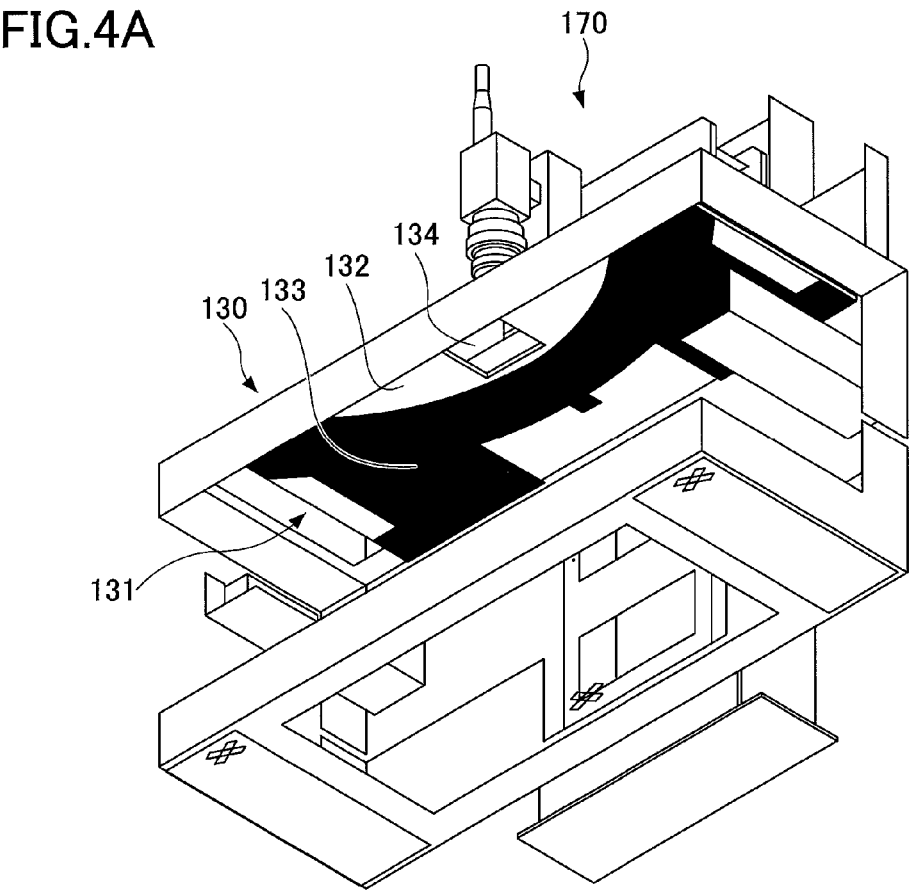
FIGS. 4A and 4B are diagrams illustrating a configuration of a reflecting surface of an illumination reflecting plate in the example of the substrate processing apparatus that includes the substrate position detecting apparatus in the first embodiment.
Figure 4B:
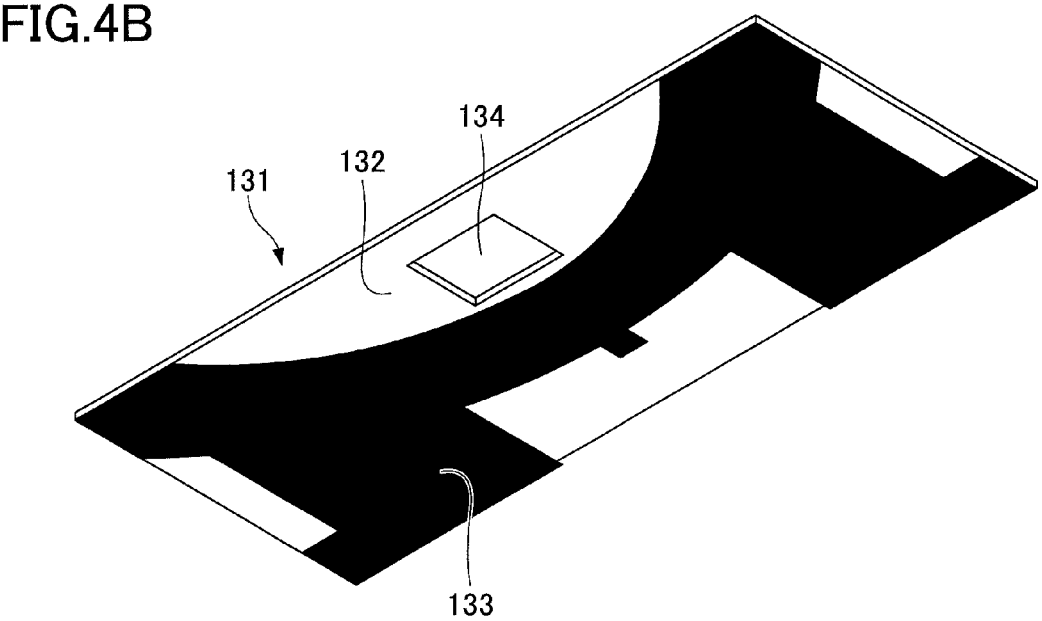

FIGS. 4A and 4B are diagrams illustrating a configuration of the reflecting surface 131 of the illumination reflecting plate 130 in the example of the substrate processing apparatus 180 that includes the substrate position detecting apparatus 170 in the first embodiment. FIG. 4A illustrates a perspective view of the example of the substrate position detecting apparatus 170 in the first embodiment viewed from under the substrate position detecting apparatus 170. FIG. 4B will be described later in the specification.

As illustrated in FIG. 4A, the illumination reflecting plate 130 may be irradiated with the light from under the illumination reflecting plate 130, and thus, the reflecting surface 131 may be provided on a lower surface of the illumination reflecting plate 130. The reflecting surface 131 may include a reflecting part 132, a reflection restricting part 133, and the opening 134. The reflecting surface 132 may form a region to reflect the light of the illumination, and irradiates the window 110 with the reflected light in order to illuminate an image pickup target. On the other hand, the reflection restricting part 133 does not reflect light of the illumination even when illuminated, in order to form a shadow at a corresponding part.

In the case in which the deposition in the substrate processing apparatus 180 is performed using the ALD or the MLD, the deposition basically occurs only on the wafer W, however, deposition may also occur on the susceptor 2 that supports the wafer W. In a case in which the deposition of a colored film occurs on the susceptor 2, the colored susceptor mark 25 may be covered thereby and become difficult to visually detect. For example, in a case in which the deposition of a TiN film occurs, the colored susceptor mark 25 formed on the susceptor 2 may no longer have a tone difference with the surrounding due to the TiN film formed thereon, and the contrast of the image picked up by the camera 140 may deteriorate.

Figure 5C:
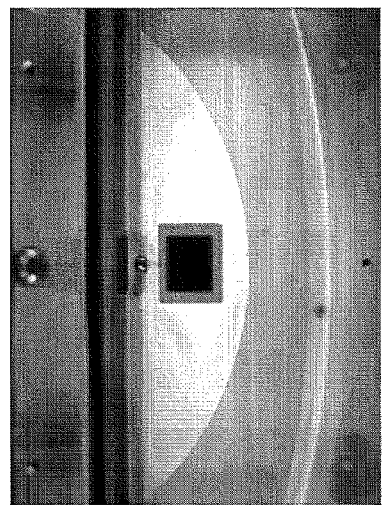
FIGS. 5A, 5B, and 5C are diagrams illustrating a picked up image of a susceptor mark according to a deposition progress state.
Figure 5B:
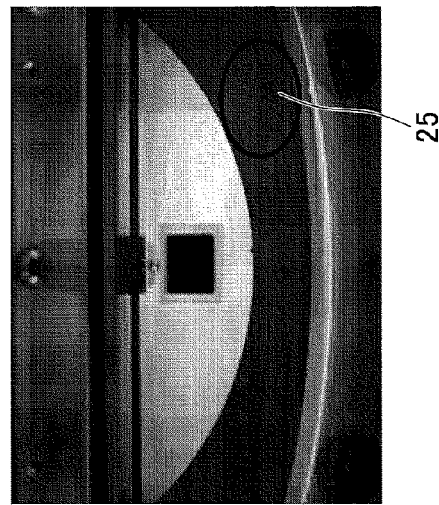
Figure 5A:
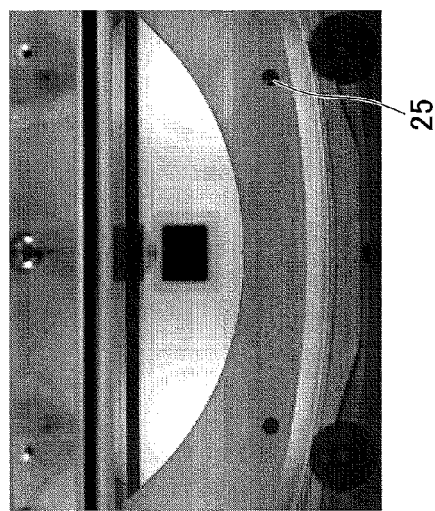

FIGS. 5A, 5B, and 5C are diagrams illustrating a picked up image of the susceptor mark according to a deposition progress state. FIG. 5A is a diagram illustrating the picked up image of the colored susceptor mark 25 in a non-deposition state in which no deposition occurs. In the non-deposition state, the colored susceptor mark 25 may be clearly visible.

FIG. 5B is a diagram illustrating the picked up image in a state in which a TiN film having a thickness on the order of 3 μm is deposited on the colored susceptor mark 25. As illustrated in FIG. 5B, when the deposition starts, the color of the susceptor 2 changes to a blackish color. Hence, the colored susceptor mark 25 also undergoes an assimilatory change to the surrounding color, thereby reducing the tone difference between the colored susceptor mark 25 and the surrounding, and the colored susceptor mark 25 becomes difficult to visually detect.

FIG. 5C is a diagram illustrating the picked up image in a state in which a TiN film having a thickness on the order of 8 μm is deposited on the colored susceptor mark 25. As illustrated in FIG. 5C, the entire picked up image appears whitish, and the colored susceptor mark 25 also becomes difficult to visually detect. As the deposition progresses, deposition in small amounts may also occur on the wall surface inside the chamber 1, and the deposition in small amounts may also occur on the inner surface of the window 110. When the TiN film that has reflectivity and does not transmit light is formed on the inner surface of the window 110, the window 110 no longer transmits light, and may act as a mirror that reflects light. As a result, the entire region of the window 110 may appear whitish in the picked up image, to deteriorate the contrast, and also make it difficult to visually detect the colored susceptor mark 25.

Returning now to the description of FIG. 4A, in the substrate position detecting apparatus 170 in the first embodiment, the reflection restricting part 133 is provided so that light is not irradiated onto the region in which the image pickup target, such as the colored susceptor mark 25, exists, in order to avoid the state illustrated in FIG. 5C. In other words, a part of the reflecting surface 131 is masked, in order to prevent reflection at the masked part. As a result, a shadow is formed in the region in which the image pickup target, such as the colored susceptor mark 25, exists, and light is not reflected from this region towards the camera 140. Consequently, the camera 140 may pick up the image with the original luminance, and an image having a suitable contrast may be acquired.

FIG. 4B is an enlarged view illustrating a part of the reflecting surface 131. The region of the reflecting surface 131 where the reflection restricting part 133 is formed may include the region in which the colored susceptor mark 25 exists. The reflection phenomenon described above occurs not only at the surface of the window 110, but also at the surface of the wafer W. The edge of the wafer W is detected when detecting the position of the wafer W, however, the edge of the wafer W cannot be detected in a case in which the light is reflected at the surface of the wafer W because the entire picked up image will appear whitish in this case. The edge of the wafer W may be detected in a case in which the wafer W is not on the susceptor 2 but is supported by a pick on a tip end of a transport arm, however, the reflection at the surface of the wafer W may make the detection of the edge of the wafer W difficult. For this reason, in the first embodiment, these phenomena are also taken into consideration, and the reflection restricting part 133 is provided in order not to irradiate the light on an edge part of the wafer W and to also form the shadow at a boundary part between the wafer W and the pick. In other words, the reflection restricting part 133 is formed between the circular reflecting part 132 formed with the opening 134 and an opposing reflecting part, so that the region of the reflection restricting part 133 includes, in addition to the colored susceptor mark 25, the boundary part between the pick and the wafer W when the wafer W is supported by the pick. Accordingly, a plurality of detecting parts that are image pickup targets may be picked up with a high contrast and detected.

The reflecting part 132 of the reflecting surface 131 may be formed by various materials, as long as the material reflects the illuminating light. For example, a thin plate made of white TEFLON (registered trademark) may be bonded to a lower surface of the illumination reflecting plate 130. In addition, the reflection restricting part 133 may be made of various materials, as long as the material does not reflect but absorbs the illuminating light. For example, the reflection restricting part 133 may be formed by a metal plate having a dull black finish or coating. The thin plate and the metal plate may be bonded separately for each region. Alternatively, the thin plate forming the reflecting part 132 may first be bonded on the entire reflecting surface 131 of the illumination reflecting plate 130, and the metal plate may then be bonded on the reflection restricting part 133 so as to mask the reflecting part 132. Various configurations may be used for the combination of the reflection restricting part 133 and the reflecting part 132, as long as the reflecting surface 131 is provided with the reflection restricting part 133 in the region that includes the image pickup target, and the reflecting part 132 is provided to secure light to be reflected in regions other than the reflection restricting part 133.

FIGS. 6A and 6B are diagrams illustrating a layout relationship of each of the marks within the chamber in the example of the substrate processing apparatus in the first embodiment. FIG. 6A illustrates the entire view of the layout of each of the marks within the chamber 1.

As illustrated in FIG. 6A, a plurality of wafers W may be set on the susceptor 2 accommodated within the chamber 1, along the circumferential direction. In the example illustrated in FIG. 6A, five (5) wafers W may be arranged on the susceptor 2. Each wafer W may be arranged within the substrate setting region 24. Two (2) colored susceptor marks 25 and two (2) cutout susceptor marks 26 are formed on the susceptor 2 in correspondence with each of the substrate setting regions 24. The layout relationship of each substrate setting region 24, the two (2) color susceptor marks 25, and the two (2) cutout susceptor marks 26 is known in advance. For this reason, the position of the wafer W may be detected by detecting the colored susceptor marks 25 and the cutout susceptor marks 26. In addition, chamber marks 18 may be provided on a surface of a bottom part 14 of the chamber 1. Two (2) chamber marks 18 may be provided only at one location, that is, at a transport opening 15 of the chamber 1 to transport the wafer W into or outside the chamber 1, in order to detect the position of the wafer W when transporting the wafer W into or outside the chamber 1. The two (2) chamber marks 18 and the two (2) colored susceptor marks 25 and the two (2) cutout susceptor marks 26 in the vicinity of the two (2) chamber marks 18 may fall inside a range 141 of the field of view of the camera 140. The cutout susceptor marks 26 will be described in more detail later in the specification.

FIG. 6B is an enlarged view of the range 141 of the field of view of the camera 140 via the window 110. As illustrated in FIG. 6B, the chamber mark 18 provided on the chamber 1, the colored susceptor mark 25 and the cutout susceptor mark 26 provided on the susceptor 2, and the substrate setting region 24 may be arranged at positions that are close to each other. In addition, the substrate position detection may be performed using the single camera 140, by arranging all of the marks 18, 25, and 26 close to each other. Furthermore, because the substrate setting region 24 is also arranged close to the marks 18, 25, and 26, even in the case in which the wafer W is supported by the pick on the tip end of the transport arm, that is an example of a substrate holding means or a substrate holding part, to transport the wafer W into or outside the chamber 1, the boundary between the wafer W and the pick may be detected.

The colored susceptor mark 25 may have an arbitrary color that is easily visible or recognizable, but may also be black, for example.

FIGS. 7A and 7B are diagrams illustrating an image of the marks picked up by a conventional substrate position detecting apparatus in comparison with an image picked up by the substrate position detecting apparatus in the first embodiment.

FIG. 7A illustrates the image of marks picked up by the conventional substrate position detecting apparatus. As illustrated in part on an enlarged scale in the lower part of FIG. 7A, the chamber mark 18 and the colored susceptor mark 25 undergo an assimilatory change to the surrounding color, thereby deteriorating the contrast and making the chamber mark 18 and the colored susceptor mark 25 difficult to visually detect.

FIG. 7B illustrates the image of marks picked up by the substrate position detecting apparatus in the first embodiment. As illustrated in part on an enlarged scale in the lower part of FIG. 7B, the chamber mark 18 and the colored susceptor mark 25 appear with a clear contrast compared to those of FIG. 7A. Hence, according to the substrate position detecting apparatus in the first embodiment, the images of the marks are acquired with a high degree of contrast, and the substrate position detection is performed positively.

Virtually all of the parts have approximately the same luminance in FIG. 7A, while white parts and black parts exist in FIG. 7B. The black parts correspond to the shadow part formed by the reflection restricting part 133. Hence, it is confirmed from FIG. 7B that the visibility of the colored susceptor mark 25 in FIG. 7B is improved compared to that in FIG. 7A.

Figure 8B:
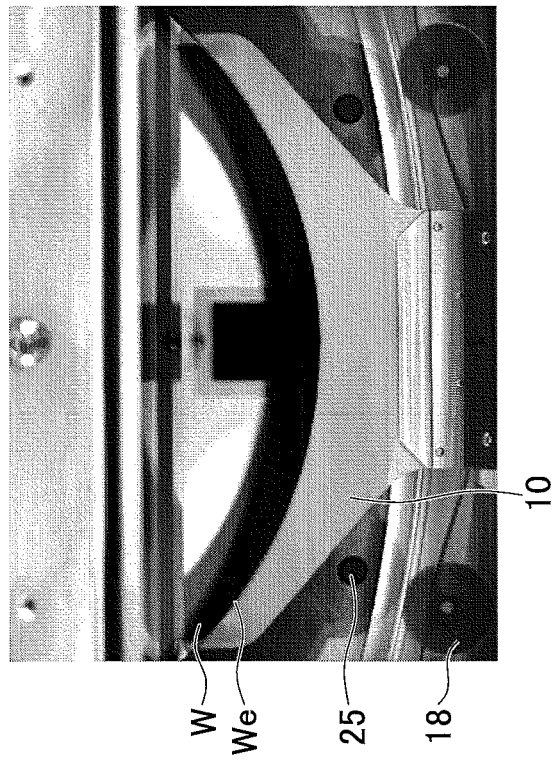
FIGS. 8A and 8B are diagrams illustrating an image of a wafer edge picked up by the conventional substrate position detecting apparatus in comparison with the image picked up by the substrate position detecting apparatus in the first embodiment.
Figure 8A:
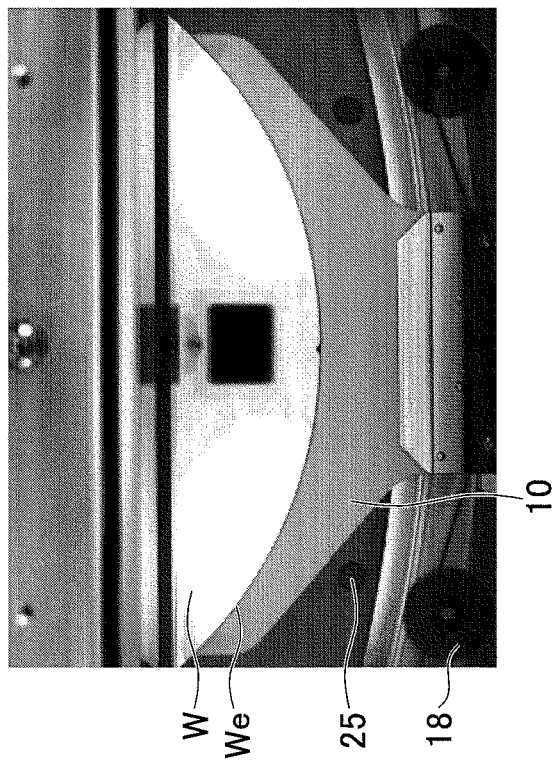

FIGS. 8A and 8B are diagrams illustrating an image of the wafer edge picked up by the conventional substrate position detecting apparatus in comparison with the image picked up by the substrate position detecting apparatus in the first embodiment.

FIG. 8A illustrates the image of the edge of the wafer W picked up by the conventional substrate position detecting apparatus. In FIG. 8A, a boundary between a pick of a transport arm 10 and the wafer W is visible to a certain extent, however, the contrast between the wafer W and the transport arm 10 (an edge We of the wafer W) is not very clear, and the edge We of the wafer W may be difficult to detect by image recognition based on a computing process.

FIG. 8B illustrates the image of the edge of the wafer W picked up by the substrate position detecting apparatus in the first embodiment. In FIG. 8B, a shadow is formed at a part corresponding to the edge We of the wafer W, and the boundary between the pick of the transport arm 10 and the wafer W appears black. In addition, the pick of the transport arm 10 appears white, such that the image of the wafer W and the transport arm 10 has a high degree of contrast. Accordingly, the edge We of the wafer W can be easily detected by an image recognition based on a computing process, and the position of the wafer W can be easily detected.

Therefore, according to the substrate position detecting apparatus in the first embodiment, the shadow may be formed without illuminating the region that includes the image pickup target, and the image pickup target may be recognized from the image having a high contrast.

Figure 9:
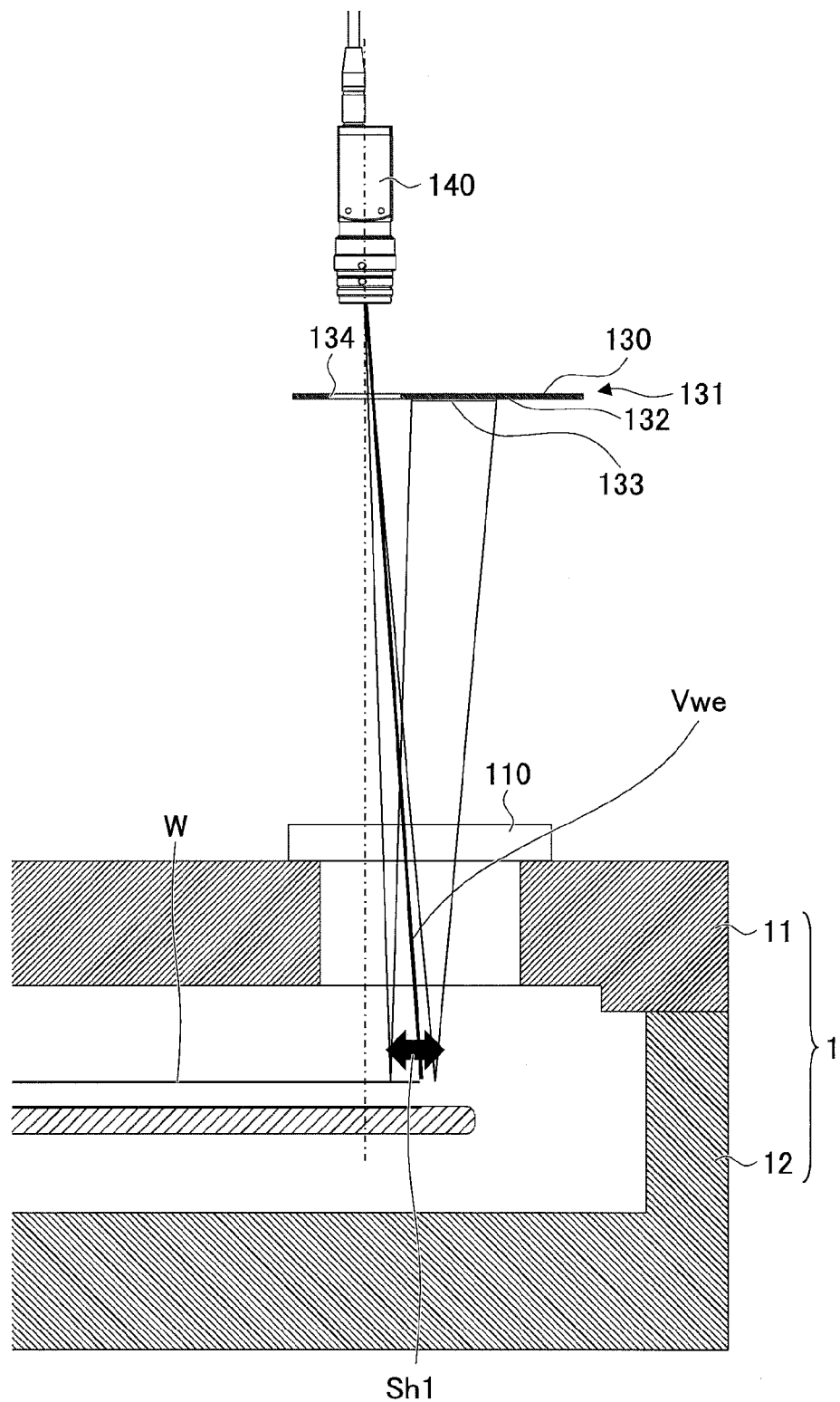
FIG. 9 is a diagram for explaining a method of setting an arrangement position of a reflection restricting part for preventing wafer reflection of the substrate position detecting apparatus in the first embodiment of the present invention.

FIG. 9 is a diagram for explaining a method of setting an arrangement position of the reflection restricting part for preventing wafer reflection of the substrate position detecting apparatus in the first embodiment of the present invention. FIG. 9 illustrates a method of setting the reflection restricting part 133 for preventing background reflection of the illuminating light (or reflection) on the wafer W. In FIG. 9, Vwe denotes a line of sight to the edge We of the wafer W. First, in FIG. 9, a predetermined region including the edge of the wafer W is set as a region Sh1 for preventing the background reflection of the illuminating light. Then, this region Sh1 is connected to a center of the field of view of the camera 140 by taking into consideration an enlargement angle of the field of view. Further, a line of sight is extended symmetrically from the region Sh1 towards the reflecting surface 131 of the illumination reflecting plate 130 by taking into consideration the enlargement angle of the field of view, in order to obtain a range to be masked on the reflecting surface 131. By providing the reflection restricting part 133 in this range to be masked, the region Sh1 including the edge We of the wafer W is not illuminated, and the shadow may be formed in the region Sh1. This range to be masked on the reflecting surface 131 of the illumination reflecting plate 130 is greater than the region Sh1 in which the background reflection of the illuminating light does not occur on the wafer W, as illustrated in FIG. 9. The reflection restricting part 133 may be set on the reflecting surface 131 of the illumination reflecting plate 130 with reference to a region of the field of view of the camera 140. As a result, the reflection restricting part 133 may be set to a suitable region, and the substrate position detection may be performed using the image recognition.

Figure 10:
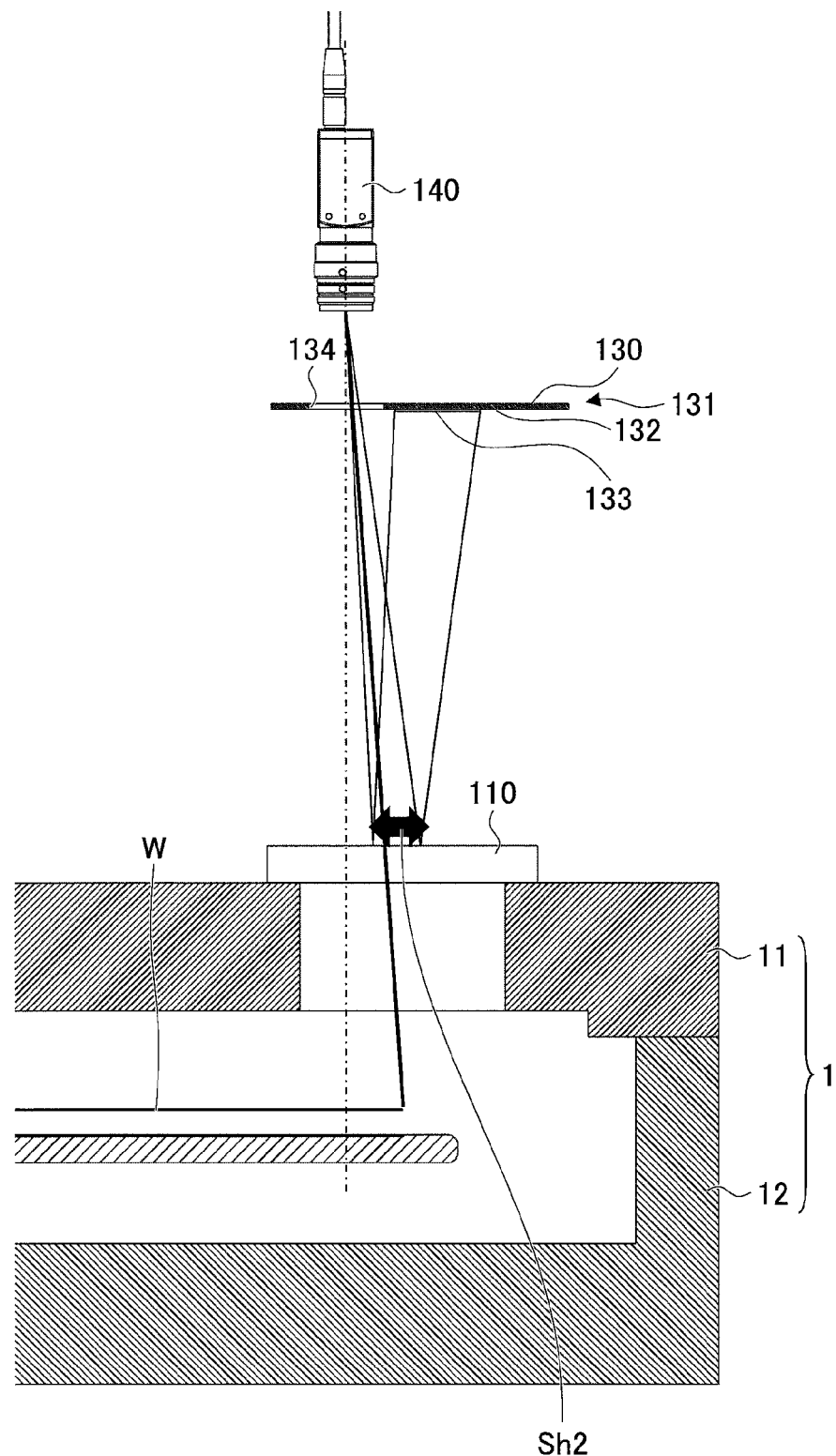
FIG. 10 is a diagram for explaining a method of setting an arrangement position of the reflection restricting part for preventing window reflection of the substrate position detecting apparatus in the first embodiment of the present invention.

FIG. 10 is a diagram for explaining a method of setting an arrangement position of the reflection restricting part for preventing window reflection of the substrate position detecting apparatus in the first embodiment of the present invention. First, in FIG. 10, a region Sh2 for preventing the background reflection of the illuminating light is set on the window 110. Then, this region Sh2 is connected to the center of the field of view of the camera 140 by taking into consideration the enlargement angle of the field of view. Further, the line of sight is extended symmetrically from the region Sh2 towards the reflecting surface 131 of the illumination reflecting plate 130 by taking into consideration the enlargement angle of the field of view, in order to obtain a range to be masked on the reflecting surface 131. The reflection restricting part 133 may be set on the reflecting surface 131 of the illumination reflecting plate 130 with reference to the region of the field of view of the camera 140, also when preventing the background reflection of the illuminating light on the window 110. As a result, the reflection restricting part 133 may be set to a suitable region so that the shadow is formed to conform to the image picked up by the camera 140.

Figure 11:
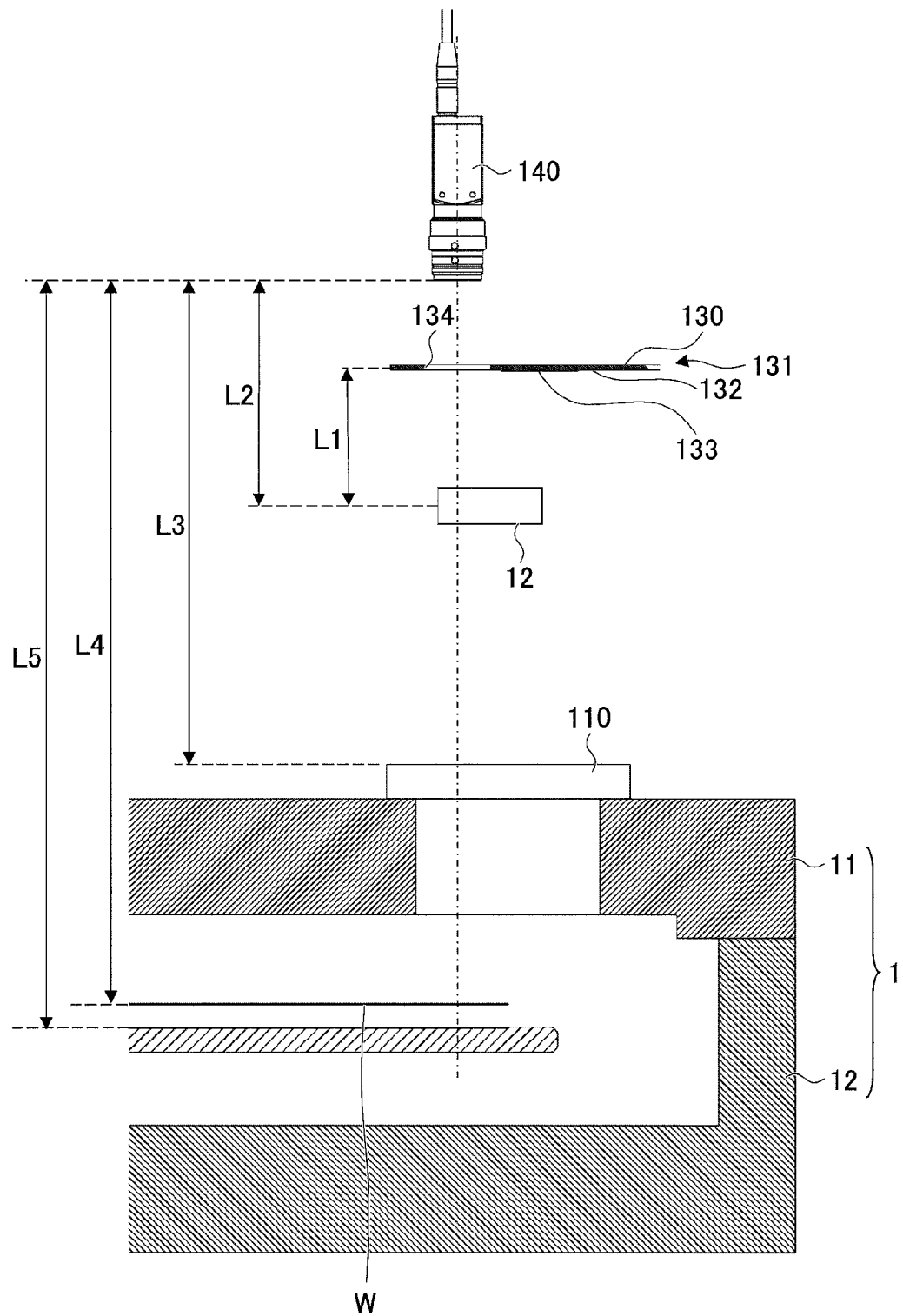
FIG. 11 is a diagram illustrating an arrangement of each of constituent elements in the example of the substrate processing apparatus and the substrate position detecting apparatus in the first embodiment of the present invention.

FIG. 11 is a diagram illustrating an arrangement of each of constituent elements in the example of the substrate processing apparatus and the substrate position detecting apparatus in the first embodiment of the present invention. FIG. 11 illustrates a distance L1 between the reflecting surface 131 of the illumination reflecting plate 130 and the illumination 120, a distance L2 between a tip end of a lens (for example, a tip end of a CCD lens) of the camera 140 and the illumination 120, a distance L3 between the tip end of the lens of the camera 140 and the window 110, a distance L4 between the tip end of the lens of the camera 140 and the surface of the wafer W, and a distance L5 between the top end of the lens of the camera 140 and the surface of the susceptor 2. For example, the reflection restricting part 133 illustrated in FIG. 10 may be set by taking into consideration the distances L1 through L5 between the constituent elements.

Hence, according to the substrate position detecting apparatus in the first embodiment, by suitably providing the reflection restricting part 133 on the reflecting surface 131 of the illumination reflecting plate 130, the reflection of the illuminating light at the surface of the window 111 and at the surface of the wafer W may be prevented, even in the case in which a deposition process is performed to deposit a film made of TiN or the like that does not transmit light, and the substrate position detection may be made to detect the position of the wafer W.

Following the above description of the substrate position detecting apparatus, a description will now be given of the substrate processing apparatus that facilitates detection of the substrate position, by improving the susceptor mark.

Figure 12B:
FIGS. 12A and 12B are diagrams illustrating an example of a contrast change of a colored susceptor mark in the conventional substrate processing apparatus for comparison purposes.
Figure 12A:
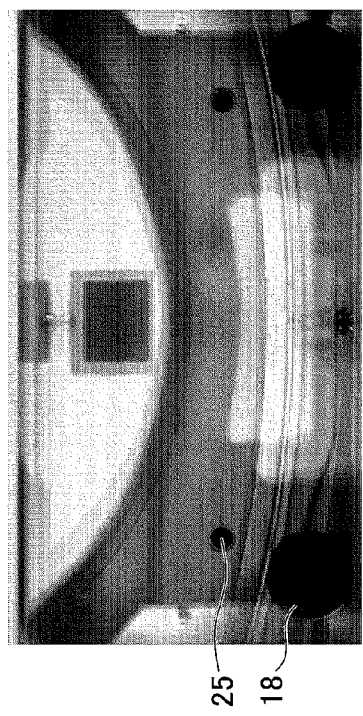

FIGS. 12A and 12B are diagrams illustrating an example of a contrast change of a colored susceptor mark in the conventional substrate processing apparatus for comparison purposes.

FIG. 12A illustrates an example of the picked up image of the colored susceptor mark before the deposition in the conventional substrate processing apparatus. As illustrated in FIG. 12A, the black colored susceptor mark 25 is visible with a high degree of contrast in the picked up image before the deposition of the TiN film.

FIG. 12B illustrates an example of the picked up image of the colored susceptor mark after the deposition in the conventional substrate processing apparatus. As illustrated in FIG. 12B, the entire picked up image appears blackish in the picked up image after the deposition, and the contrast is low, thereby making it difficult to recognize the colored susceptor mark 25 after the deposition.

Accordingly, the substrate processing apparatus in the first embodiment provides the cutout susceptor mark 26 in addition to the colored susceptor mark 25.

Returning now to the description of FIG. 6B, FIG. 6B illustrates a top view of the cutout susceptor marks 26. The cutout susceptor mark 26 may be formed by cutting out a part of the susceptor 2. The function of the cutout susceptor mark 26 is achieved as long as a hole or cutout is formed in the susceptor 2, and the cutout susceptor mark 26 may be provided at arbitrary positions on the susceptor 2. However, when the ease of forming the cutout susceptor mark 26 is taken into consideration, the cutout susceptor mark 26 may preferably be provided at an edge part of the susceptor 2. In other words, the edge part of the susceptor 2 may preferably be cutout to form the cutout susceptor mark 26, in a manner similar to forming a notch in the wafer W. The cutout susceptor mark 26 may be formed to various shapes, and for example, the susceptor 2 may be cutout to an approximately cylindrical shape in order to form the cutout susceptor mark 26. FIG. 6B illustrates an example in which the cutout susceptor mark 26 is cutout to a cylindrical shape.

Figure 13B:
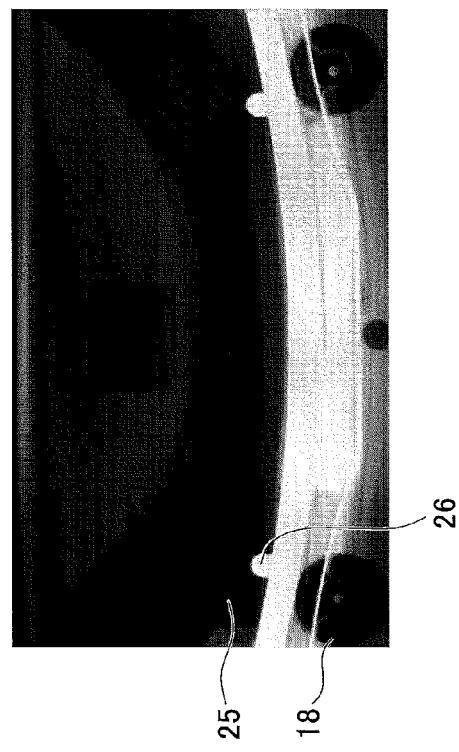
FIGS. 13A and 13B are diagrams illustrating an example of a contrast change of a cutout susceptor mark in the substrate processing apparatus in the first embodiment of the present invention.
Figure 13A:
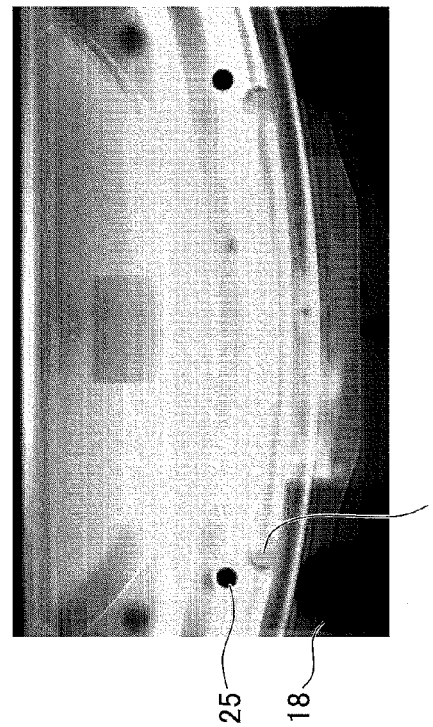

FIGS. 13A and 13B are diagrams illustrating an example of a contrast change of a cutout susceptor mark in the substrate processing apparatus in the first embodiment of the present invention.

FIG. 13A illustrates an example of the picked up image of the cutout susceptor mark before the deposition in the substrate processing apparatus in the first embodiment. As illustrated in FIG. 13A, before the deposition, the colored susceptor mark 25 has a degree of contrast higher than that of the cutout susceptor mark 26 in the picked up image.

FIG. 13B illustrates an example of the picked up image of the cutout susceptor mark after the deposition in the substrate processing apparatus in the first embodiment. As illustrated in FIG. 13B, after the deposition, the colored susceptor mark 25 undergoes an assimilatory change to the surrounding black color and the degree of contrast is low in the picked up image. On the other hand, the cutout susceptor mark 26 becomes white and conspicuous from the black color surrounding and the degree of contrast is high in the picked up image, thereby enabling easy recognition of the cutout susceptor mark 26. Hence, in the state in which the TiN film or the like is formed, the cutout susceptor mark 26 may display a high degree of contrast in the picked up image, and the cutout susceptor mark 26 may be extremely effective for use in the image recognition.

Therefore, in the substrate processing apparatus in the first embodiment, a part of the susceptor 2, typically the edge part of the susceptor 2, may be cut out to form the cutout susceptor mark 26, separately from the colored susceptor mark 25, in order to enable stable detection of the mark even at the time of the deposition. Because the colored susceptor mark 25 is formed on the surface of the susceptor 2, the contrast of the colored susceptor mark 25 in the picked up image may become low when the color of the entire surface of the susceptor 2 becomes the same, and it may be difficult to stably detect the color susceptor mark 25. However, in the substrate processing apparatus in the first embodiment, the cutout susceptor mark 26 is provided at the edge part of the susceptor 2, and the degree of contrast of the cutout susceptor mark 26 with respect to the lower part of the susceptor 2 not subjected to the deposition becomes high, this enabling positive detection of the cutout susceptor mark 26.

However, as illustrated in FIG. 13A, the colored susceptor mark 25 may have a low degree of contrast in the state before the deposition, that is, before coloring. Hence, both the colored susceptor mark 25 and the cutout susceptor mark 26 may be used, and the colored susceptor mark 25 may preferably be the detection target in a state before the deposition or in a case in which the deposition process deposits a film having a light tone and a light color, and the cutout susceptor mark 26 may preferably be the detection target in a case in which the deposition process deposits a film having a dark tone. In this case, as described above in conjunction with FIG. 1, the susceptor mark selection judging part 161 and/or the susceptor mark selection switch 162 may preferably be provided within the processing part 160 or externally to the processing part 160, in order to detect the position of the susceptor 2 by automatically or manually switching between the susceptor marks 25 and 26.

The cutout susceptor mark 26 may be provided if necessary. In a case in which the substrate position detection may be performed positively using only the colored susceptor mark 25, the cutout susceptor mark 26 may be omitted.

Second Embodiment

Figure 14A:
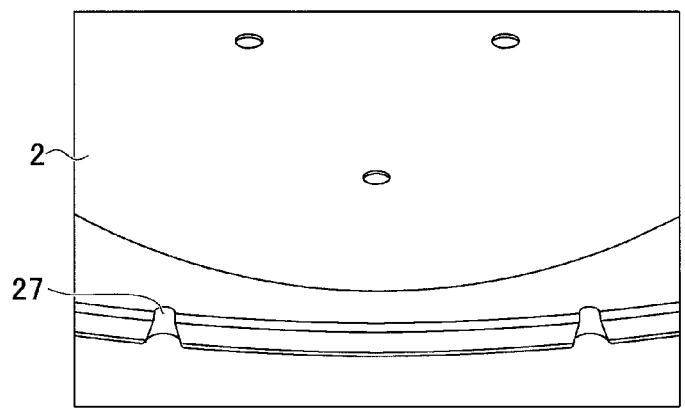
FIGS. 14A, 14B, and 14C are diagrams illustrating an example of the substrate processing apparatus in a second embodiment of the present invention.
Figure 14B:
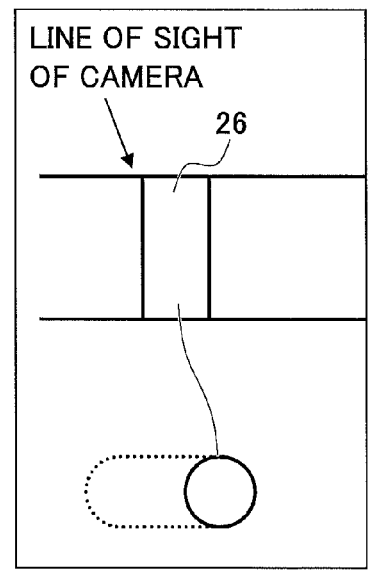
Figure 14C:
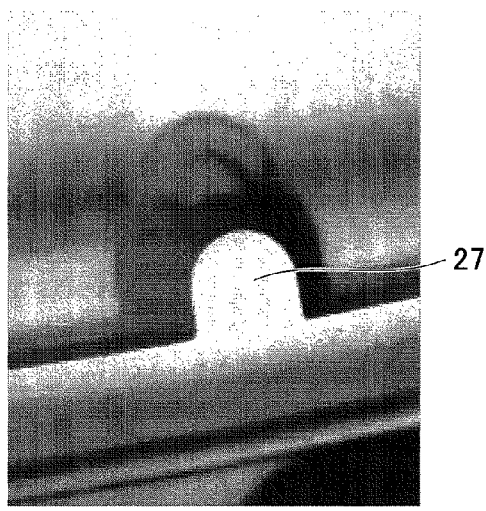

FIGS. 14A, 14B, and 14C are diagrams illustrating an example of the substrate processing apparatus in a second embodiment of the present invention. FIG. 14A is a perspective view of an example of the susceptor 2 of the substrate processing apparatus in the second embodiment. In FIG. 14A, cutout susceptor marks 27 are formed at the edge part of the susceptor 2. In the substrate processing apparatus in the second embodiment, the shape of the cutout susceptor mark 27 is not a simple cylindrical shape, but the shape is tapered such that the diameter increases from the top surface towards the bottom surface of the susceptor 2.

FIG. 14B is a diagram for explaining differences between the cutout susceptor mark 27 having the tapered shape, and the cutout susceptor mark 26 having the cylindrical shape. In the case of the cutout susceptor mark 26 having the simple cylindrical shape illustrated in FIG. 14B, if the camera 140 has an angle of visibility, the curved shape at the top surface of the cutout susceptor mark 26 is picked up together with the sidewall within the cylindrical shape. In this case, a boundary between the curved shape and the sidewall may become difficult to recognize, and there is a possibility of not accurately recognizing the curved shape of the cutout susceptor mark 26 by image recognition. Generally, in the case of the susceptor mark having the circular shape, a center of the circular shape is measured in order to measure the coordinates of the susceptor mark, and thus, inaccurate recognition of the curved shape of the cutout susceptor mark 26 may result in undesirable consequences.

Accordingly, in the substrate processing apparatus in the second embodiment, the cutout susceptor mark 27 may have a tapered shape having an angle (or taper angle) greater than the angle of visibility of the camera 140 as illustrated in FIG. 14A (or greater than an incident angle of the light from the illumination reflecting plate 130), in order to positively prevent erroneous recognition of the cutout susceptor mark 27.

FIG. 14C is a diagram illustrating an example of the picked up image of an example of the cutout susceptor mark 27 of the substrate processing apparatus in the second embodiment. As illustrated in FIG. 14C, the circular edge of the cutout susceptor mark 27 can be recognized accurately, and the position of the susceptor 2 can be detected with ease.

Constituent elements of the substrate processing apparatus in the second embodiment, other than the cutout susceptor mark 27 and including the substrate position detecting apparatus 170, may be similar to the corresponding constituent elements of the substrate processing apparatus in the first embodiment, and a description thereof have been omitted.

According to the substrate processing apparatus in the second embodiment, the cutout susceptor mark 27 can be recognized positively, and the substrate position detection can be performed accurately.

Third Embodiment

Next, a description will be given of a third embodiment of the present invention. In the third embodiment, the substrate detecting apparatus in the first embodiment may be formed as an ALD apparatus or an MLD apparatus that deposits a TiN film, for example.

Returning now to the description of FIG. 1, FIG. 1 is also a cross sectional view illustrating an example of a deposition apparatus in the third embodiment applied with the substrate position detecting apparatus 170 in the first embodiment of the present invention. A deposition apparatus 200 in the third embodiment of the present invention may include the chamber 1 having a generally circular and flat shape in the plan view, and the susceptor 2 provided within the chamber 1 and having a center of rotation matching the center of the chamber 1, as illustrated in FIG. 1. The chamber 1 may be configured so that the top plate 11 is separable from the container body 12. The top plate 11 may be pushed against the container body 12 via a sealing member such as the O-ring 13, for example, according to a decompression state inside the chamber 1, in order to hermetically seal the chamber 1. On the other hand, when the top plate 11 needs to be separated from the container body 12, a driving mechanism (not illustrated) may be used to push the top plate 11 upwards.

In addition, the hole 16 that forms the opening may be provided in the top plate 11. The window 110 may be provided on the top surface of the top plate 11 to oppose the hole 16 and seal the chamber 1. The substrate position detecting apparatus 170 may be detachably mounted on the window 110. The configuration of the substrate position detecting apparatus 170 may be as described above. The position of the wafer W set on the susceptor 2 within the deposition apparatus 200 may be detected by executing a substrate position detection method using the substrate position detecting apparatus 170 in the third embodiment of the present invention. The susceptor 2 may be provided with the colored susceptor marks 25, and the cutout susceptor marks 26 or the cutout susceptor marks 27 may be provided if necessary.

A central part of the susceptor 2 may be fixed to a core part 21 having a cylindrical shape, and this core part 21 may be fixed to an upper end of the rotational shaft 22 extending in the vertical direction. The rotational shaft 22 may penetrate the bottom part 14 of the container body 12, and a lower end of the rotational shaft 22 may be mounted on a driving part 23 that rotates the rotational shaft 22 about a vertical axis in a clockwise direction in this example. The rotational shaft 22 and the driving part 23 may be accommodated within a case body 20 having a hollow cylindrical shape with an upper surface that is open. The case body 20 may be sealed and mounted on a lower surface of the bottom part 14 of the chamber 1 via a flange part 20a that is provided on the upper surface of the case body 20. Hence, an internal atmosphere of the case body 20 may be isolated from an external atmosphere of the case body 20. In addition, the chamber mark 18 may be provided on the surface of the bottom part 14 of the chamber 1.

Figure 15:
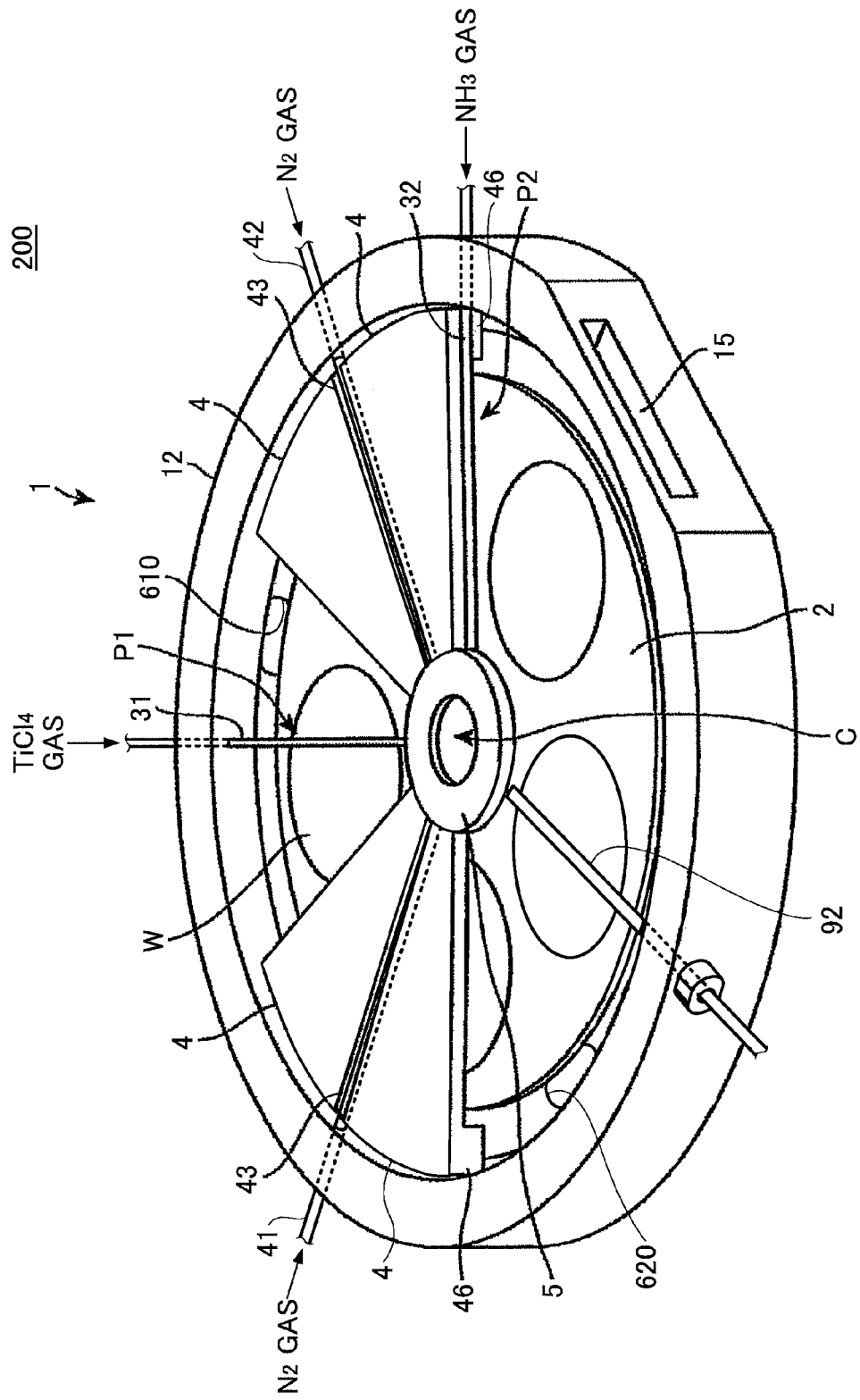
FIG. 15 is a perspective view illustrating a deposition apparatus in a third embodiment of the present invention.
Figure 16:
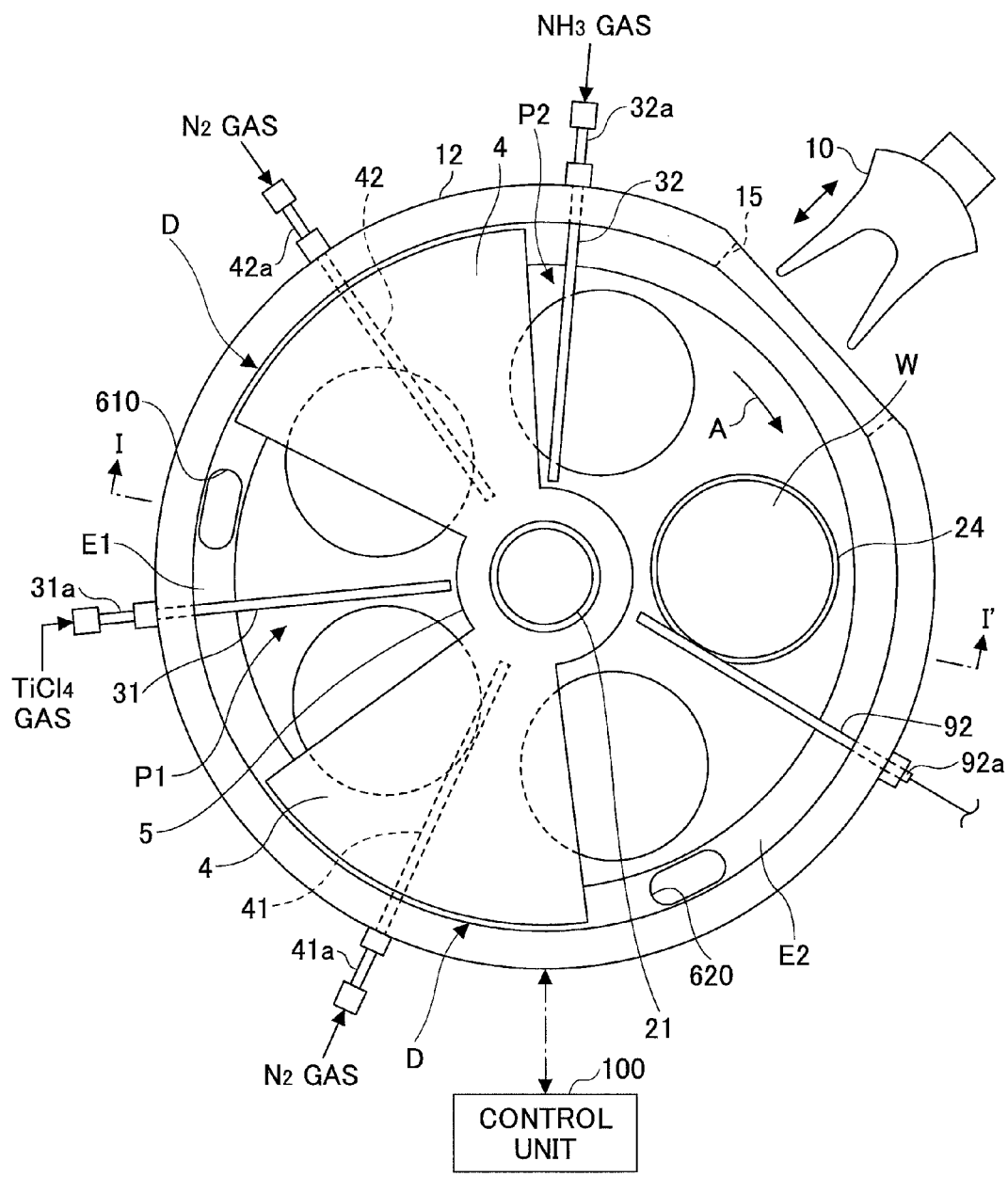
FIG. 16 is a plan view schematically illustrating a configuration within a vacuum container of the deposition apparatus in the third embodiment of the present invention.

FIG. 15 is a perspective view illustrating the deposition apparatus in the third embodiment of the present invention. FIG. 16 is a plan view schematically illustrating a configuration within a vacuum container of the deposition apparatus in the third embodiment of the present invention.

As illustrated in FIGS. 15 and 16, a plurality of recesses (or substrate setting regions) 24 may be provided on a surface part of the rotary table (or susceptor) 2 along a rotating direction (or circumferential direction). A plurality of wafers W are set in the recesses 24, and five (5) wafers W may be set in this example. For the sake of convenience, the wafer W is set only in one recess 24 illustrated in FIG. 15. The recess 24 may have an inner diameter slightly greater than that of the wafer W by 4 mm, for example, and a depth approximately the same as a thickness of the wafer W. Accordingly, when the wafer W is accommodated within the recess 24, the surface of the wafer W and the surface of the rotary table 2 (the surface region of the rotary table 2 where the wafer W is not set) may have the same height. For example, three (3) penetration holes (not illustrated) may be formed in a bottom surface of the recess 24, and elevator pins (not illustrated) that support the back surface of the wafer W and raise and lower the wafer W may penetrate the penetration holes.

FIGS. 15 and 16 are diagrams for explaining the configuration inside the chamber 1, and the illustration of the top plate 11 is omitted for the sake of convenience. As illustrated in FIGS. 15 and 16, a reaction gas nozzle 31, a reaction gas nozzle 32, and separation gas nozzles 41 and 42 respectively made of quartz, for example, may be arranged above the rotary table 2 at intervals along the circumferential direction of the chamber 1. The circumferential direction of the chamber is a rotating direction of the rotary table 2 indicated by an arrow A in FIG. 16. In the example illustrated in FIGS. 15 and 16, the separation gas nozzle 41, the reaction gas nozzle 31, the separation gas nozzle 42, and the reaction gas nozzle 32 may be arranged in this order along a clockwise direction (that is, the rotating direction of the rotary table 2) from the transport opening 15 that will be described later in the specification. Gas inlet ports 31a, 32a, 41a, and 42a at base end parts of the nozzles 31, 32, 41, and 42 illustrated in FIG. 16 may be fixed to an outer peripheral wall of the container body 12, so that the nozzles 31, 32, 41, and 42 are introduced into the chamber from the outer peripheral wall of the chamber 1 and extend horizontally with respect to the rotary table 2 along a radial direction of the container body 12.

In the third embodiment, the reaction gas nozzle 31 may be connected to a titanium chloride ($TiCl_4$) gas supply source (not illustrated), via piping, a flow controller, and the like (each not illustrated). The reaction gas nozzle 32 may be connected to an ammonia ($NH_3$) gas supply source (not illustrated), via piping, a flow controller, and the like (each not illustrated). Each of the separation gas nozzles 41 and 42 may be connected to a separation gas supply source (not illustrated), via piping, a flow controller, and the like (not illustrated). The separation gas may be a noble gas such as helium (He), argon (Ar), or the like, or an inert gas such as nitrogen ($N_2$) gas, or the like. In the third embodiment, $N_2$ gas is used as the separation gas for the sake of convenience.

Each of the reaction gas nozzles 31 and 32 may include a plurality of gas ejecting holes 33 that open towards the rotary table 2. The gas ejecting holes 33 may be arranged at intervals of 10 mm, for example, along a longitudinal direction of each of the reaction gas nozzles 31 and 32. A region below the reaction gas nozzle 31 may form a first processing region P1 for adsorption of $TiCl_4$ gas on the wafer W. A region below the reaction gas nozzle 32 may form a second processing region P2 for nitriding the TiCl4 gas adsorbed on the wafer W in the first processing region P1.

As the wafer W rotates and successively passes the first processing region P1 supplied with the $TiCl_4$ gas and the second processing region P2 supplied with $NH_3$ gas, adsorption of the $TiCl_4$ gas and the adsorption of the $NH_3$ gas onto the surface of the wafer W may successively occur, to thereby deposit a molecular layer of TiN on the surface of the wafer W. In addition, a molecular layer of TiN may also be deposited on the inner surface of the window 110.

However, even if the TiN film is deposited on the window 110, the substrate position detecting apparatus 170 may have the configuration and function to accurately detect the position of the wafer W, similarly to the first embodiment described above.

As illustrated in FIGS. 15 and 16, two convex parts 4 are provided within the chamber 1. The convex parts 4 may form a separation region D together with the separation gas nozzles 41 and 42, and thus, the two convex parts 4 may be mounted on a back surface of the top plate 11 so as to project towards the rotary table 2, as will be described later. In addition, each convex part 4 may have a fan shape that has its vertex parts cut into an arcuate shape in a plan view. In the third embodiment, an inner arcuate part of the fan-shaped convex part 4 may connect to a projecting part 5 that will be described later in the specification, and an outer arcuate part of the fan-shaped convex part 4 may be arranged along the inner peripheral surface of the container body 12 of the chamber 1.

Figure 17:
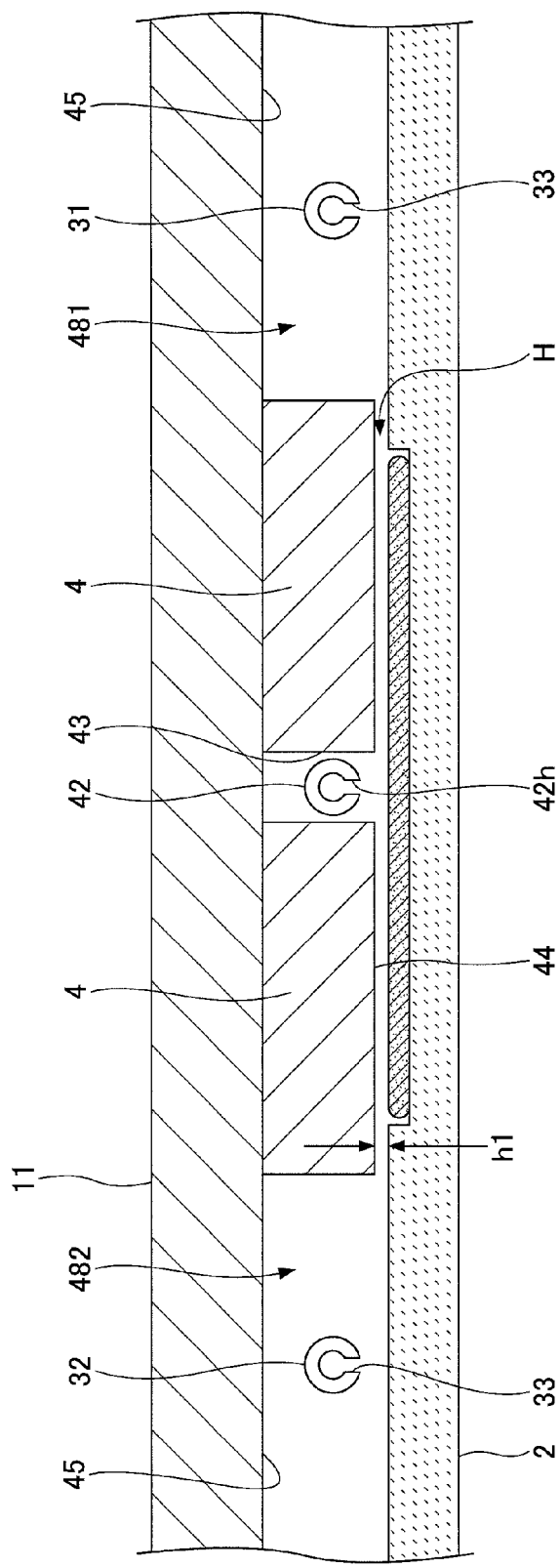
FIG. 17 is a cross sectional view schematically illustrating the vacuum container along a concentric circle with respect to a rotary table that is rotatably provided within the vacuum container of the deposition apparatus in the third embodiment of the present invention.

FIG. 17 is a cross sectional view schematically illustrating the vacuum container along a concentric circle with respect to the rotary table that is rotatably provided within the vacuum container of the deposition apparatus in the third embodiment of the present invention. FIG. 17 illustrates the cross section along the concentric circle with respect to the rotary table 2, from the reaction gas nozzle 31 to the reaction gas nozzle 32. As illustrated in FIG. 17, because the convex parts 4 are mounted on the back surface of the top plate 11, a flat and low ceiling surface (or first ceiling surface) 44 formed by a lower surface of the convex part 4, and a ceiling surface (or second ceiling surface) 45 higher than the ceiling surface 44 and arranged on both sides of the ceiling surface 44 along the circumferential direction may be formed within the chamber 1. The ceiling surface 44 has a fan shape with its vertex parts cut into an arcuate shape in a plan view. In addition, as illustrated in FIG. 17, one of the convex parts 4 may include a groove part 43 that extends in the radial direction and is arranged at a center along the circumferential direction. The separation gas nozzle 42 may be accommodated within the groove part 43. The other convex parts 4 may include a similar groove part 43, and the separation gas nozzle 41 may be accommodated within the groove part 43 of this other convex part 4. The reaction gas nozzles 31 and 32 may be arranged in spaces below the higher, ceiling surfaces 45. The reaction gas nozzles 31 and 32 may be separated from the ceiling surface 45 and provided in a vicinity of the wafer W. For the sake of convenience, in FIG. 17, the space below the ceiling surface 45 where the reaction gas nozzle 31 may be provided is denoted by the reference numeral 481, and the space below the ceiling surface 45 where the reaction gas nozzle 32 may be provided is denoted by the reference numeral 482.

Each of the separation gas nozzles 41 and 42 accommodated within the groove parts 43 of the convex parts 4 may include a plurality of gas ejecting holes that open towards the rotary table 2, and FIG. 17 illustrates gas ejecting holes 42h of the separation gas nozzle 42. The gas ejecting holes 42h may be arranged at intervals of 10 mm, for example, along a longitudinal direction of each of the separation gas nozzles 41 and 42.

The ceiling surface 44 may form a narrow separation space H with respect to the rotary table 2. When $N_2$ gas is supplied from the gas ejection holes 42h of the separation gas nozzle 42, the $N_2$ gas may pass through the separation space H and flow towards the spaces 481 and 482. In this state, a volume of the separation space H is smaller than volumes of the spaces 481 and 482, and thus, the $N_2$ gas may make the pressure in the separation space H higher than the pressures in the spaces 481 and 482. In other words, the separation space H having the higher pressure may be formed between the spaces 481 and 482. In addition, the $N_2$ gas flowing from the separation space H to the spaces 481 and 482 may act as a counter flow with respect to the $TiCl_4$ gas from the first region P1 and the $NH_3$ gas from the second region P2. Accordingly, the $TiCl_4$ gas from the first region P1 and the $NH_3$ gas from the second region P2 may be separated by the separation space H. Consequently, the $TiCl_4$ gas and the $NH_3$ gas may be prevented from mixing and reacting with each other within the chamber 1.

A height h1 of the ceiling surface 44 with respect to an upper surface of the rotary table 2 may preferably be set to a suitable value in order to make the pressure in the separation space H higher than those in the spaces 481 and 482, by taking into consideration a pressure within the chamber 1 at the time of the deposition, a rotational speed of the rotary table 2, an amount of the separation gas ($N_2$ gas) to be supplied, and the like.

On the other hand, the projecting part 5 that surrounds an outer periphery of the core part 21 on which the rotary table 2 is fixed may be provided on the back surface of the top plate 11, as illustrated in FIGS. 15 and 16. In the third embodiment, the projecting part 5 may be formed in continuous with a part of the projecting part 4 on the side at the center of rotation, and a lower surface of the projecting part 5 may be formed to the same height as the ceiling surface 44.

Figure 18:
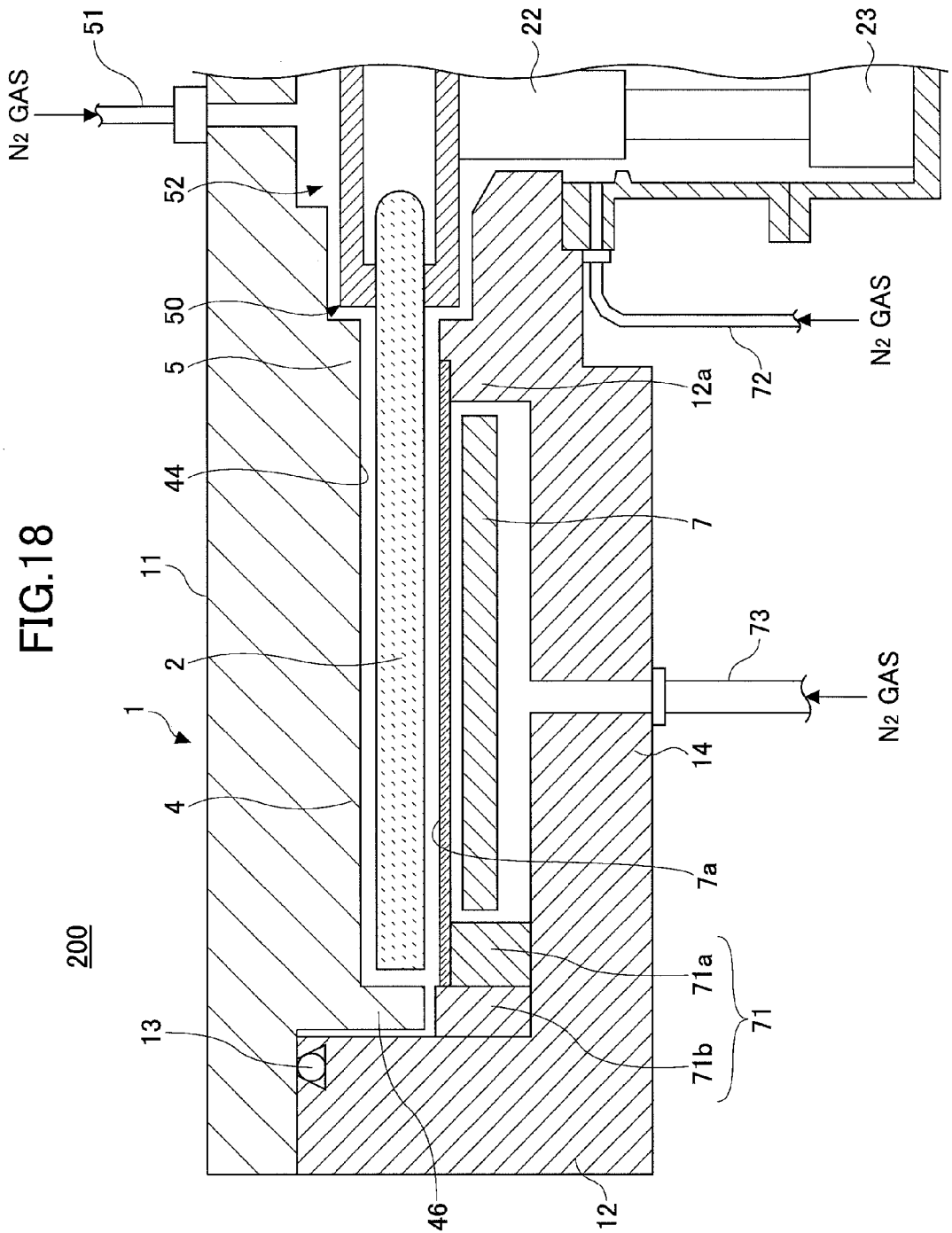
FIG. 18 is another cross sectional view schematically illustrating the deposition apparatus in the third embodiment of the present invention.

FIG. 1 may be the cross sectional view taken along a line I-I' in FIG. 16 to illustrate the region where the ceiling surface 45 is provided. On the other hand, FIG. 18 is another cross sectional view schematically illustrating the deposition apparatus in the third embodiment of the present invention. FIG. 18 illustrates the cross section of the region where the ceiling surface 44 is provided. As illustrated in FIG. 18, an L-shaped part 46 opposing an outer edge surface of the rotary table 2 may be formed on a peripheral edge part of the fan-shaped convex part 4 (that is, at a part on the outer edge side of the chamber 1). The L-shaped part 46 may suppress the intrusion of the separation gas from both sides of the separation region D, similarly to the convex parts 4, and suppress mixing of the two reaction gases. Because the fan-shaped convex part 4 is provided on the top plate 11 and the top plate 11 is removable from the container body 12, a slight gap may be formed between an outer peripheral surface of the L-shaped part 46 and the container body 12. A gap between an inner peripheral surface of the L-shaped part 46 and the outer edge surface of the rotary table 2, and a gap between the outer peripheral surface of the L-shaped part 46 and the container body 12 may be set to dimensions similar to the height of the ceiling surface 44 with respect to the upper surface of the rotary table 2.

The inner peripheral wall of the container body 12 may be formed as a vertical surface in the separation region D, adjacent to the outer peripheral surface of the L-shaped part 46, as illustrated in FIG. 17. However, the inner peripheral wall of the container body 12 in parts other than the separation region D may have a concave shape that curves outwardly, from a part opposing the outer edge surface of the rotary table 2 to the bottom part 14, as illustrated in FIG. 1. For the sake of convenience, this part of the inner peripheral wall of the container body 12 having the concave shape with an approximately rectangular cross section will be referred to as an "exhaust region". More particularly, the exhaust region communicating to the first processing region P1 will be referred to as a first exhaust region E1, and the exhaust region communicating to the second processing region P2 will be referred to as a second exhaust region E2. As illustrated in FIGS. 1 and 16, a first exhaust vent 610 and a second exhaust vent 620 may be formed at bottom parts of the first exhaust region E1 and the second exhaust region E2, respectively. As illustrated in FIG. 1, the first exhaust vent 610 and the second exhaust vent 620 may be connected to a vacuum pump 640 via exhaust pipes 630, respectively. The vacuum pump 640 is an example of a vacuum exhaust means or a vacuum exhaust device. In FIG. 1, a pressure controller 650 may be connected to the exhaust pipes 630.

A heater unit 7, that is an example of a heating means or a heating device, may be provided in the space between the rotary table 2 and the bottom part 14 of the chamber 1, as illustrated in FIGS. 1 and 18. The heater unit 7 may heat the wafer W on the rotary table 2 to a temperature (for example, 400° C.) determined by a process recipe, via the rotary table 2. A ring-shaped cover member 71 illustrated in FIG. 18 may be provided on the lower side in the vicinity of the peripheral edge of the rotary table 2, in order to partition the atmosphere from the space above the rotary table 2 to the exhaust regions E1 and E2 and the atmosphere in which the heater unit 7 is provided, and suppress intrusion of gas into the region under the rotary table 2. The cover member 71 may include an inner side member 71a and an outer side member 71b. The inner side member 71 may be provided below the rotary table 2 in a region corresponding to the outer edge part of the rotary table 2 and an outer peripheral region on the outer side of the outer edge part of the rotary table 2. The outer side member 71b may be provided between the inner side member 71a and the inner wall surface of the chamber 1. The outer side member 71b may be provided adjacent to the L-shaped part 46 in the separation region D below the L-shaped part 46 that is formed on the outer edge part of the convex part 4. On the other hand, the inner side member 71a may surround the entire periphery of the heater unit 7 below the outer edge part of the rotary table 2 (and below a part slightly on the outer side of the outer edge part of the rotary table 2).

A part of the bottom part 14 closer to the center of rotation than the space in which the heater unit 7 is arranged may form a projecting part 12a that projects upwardly to become adjacent to the core part 21 in the vicinity of the central part on the lower surface of the rotary table 2. A narrow space may be formed between the projecting part 12a and the core part 21. In addition, a narrow gap may be formed between the rotational shaft 22 and an inner peripheral surface forming a penetration hole for the rotational shaft 22 and penetrating the bottom part 14. This narrow space and narrow gap may communicate to the case body 20. A purge gas supply pipe 72 may be provided on the case body 20 in order to supply a purge gas such as $N_2$ gas to the narrow space and narrow gap to purge. A plurality of purge gas supply pipes 73 for purging the space in which the heater unit 7 is arranged may be provided in the bottom part 14 of the chamber 1 under the heater unit 7 at predetermined angular intervals along the circumferential direction. FIG. 18 illustrates one of the purge gas supply pipes 73 for the sake of convenience. Further, a lid member 7a that covers from the inner peripheral wall (upper surface of the inner side member 71a) of the outer side member 71b to the upper end part of the projecting part 12a along the circumferential direction, may be provided in order to suppress intrusion of gas into the region in which the heater unit 7 is provided. The lid member 7a may be made of quartz, for example.

A separation gas supply pipe 51 may be connected to a central part of the top plate 11 of the chamber 11, in order to supply the separation gas, that is $N_2$ gas in this example, to a space 52 between the top plate 11 and the core part 21. The separation gas supplied to this space 52 may be ejected towards the peripheral edge of the rotary table 2 along the surface on the side of the substrate setting region 24 of the rotary table 2, via a narrow gap between the projecting part 5 and the rotary table 2. The pressure in the space 50 may be maintained higher than those in the spaces 481 and 482 by the separation gas. Accordingly, the space 50 may suppress mixing of the TiCl4 gas supplied to the first processing region P1 and the NH3 gas supplied to the second processing region P2 through a central region C. In other words, the space 50 (or the center region C) may function similarly to the separation space H (or the separation region D).

In addition, as illustrated in FIGS. 15 and 16, the transport opening 15 through which the wafer W is exchanged between the external transport arm 10 and the rotary table 2 may be formed in the sidewall of the chamber 1. This transport opening 15 may be opened and closed by a gate valve (not illustrated). Because the wafer W is exchanged between the external transport arm 10 and the rotary table 2 in a state in which the recess (or substrate setting region) 24 of the rotary table 2 is located at a position corresponding to the transport opening 15, the three (3) penetration holes (not illustrated) may be formed in the bottom surface of the recess 24, and the elevator pins (not illustrated) that support the back surface of the wafer W and raise and lower the wafer W through the penetration holes and an elevator mechanism (not illustrated) that raises and lowers the elevator pins may be provided under the rotary table 2 at the position where the exchange of the wafer W takes place between the external transport arm 10 and the rotary table 2.

In addition, a control unit 100 may be provided in the deposition apparatus in the third embodiment, as illustrated in FIG. 1. The control unit 100 is an example of a computer, such as a CPU (Central Processing Unit), that controls the operation of the entire deposition apparatus 200. The control unit 100 may include a memory that stores a program which, when executed by the control unit 100, causes the control unit 100 to execute a deposition process in the deposition apparatus 200 according to a deposition method under the control of the control unit 100. The program may include program steps to execute the deposition process or deposition method. The program may be stored in a recording medium such as a hard disk, a compact disk, a magneto-optical disk, a memory card, a flexible disk, and the like. The program stored in the recording medium may be read by a read unit (not illustrated) and installed into the memory of the control unit 100, for example.

The control unit 100 may also control the processing part 160, the susceptor mark selection judging part 161, and the like.

The substrate position detecting apparatus and the substrate processing apparatus described in conjunction with the first embodiment may be applied to the deposition apparatus described in conjunction with the third embodiment to deposit a colored film having reflectivity, such as a TiN film and the like, using the ALD or the MLD. In addition, the image pickup target may be picked up with a high degree of contrast when depositing the colored film having reflectivity, such as the TiN film and the like, and the position of the wafer W may be detected accurately and positively based on the picked up image.

The substrate position detecting apparatus 170 and the substrate processing apparatus 180 in the first embodiment are applied to the deposition apparatus 200 in the third embodiment. However, the substrate processing apparatus 180 in the second embodiment may of course be applied to the deposition apparatus 200 in the third embodiment.

According to the described embodiments, the image pickup target within the chamber may be picked up with a high degree of contrast, in order to detect the position of the substrate.

Although the embodiments are numbered with, for example, "first," "second," or "third," the ordinal numbers do not imply priorities of the embodiments.

Further, the present invention is not limited to the above embodiments, and various variations and modifications may be made without departing from the spirit and scope of the present invention.

What is claimed is:

1. A substrate position detecting apparatus that detects a position of a substrate inside a chamber from an image of a target inside the chamber, comprising:
   an imager provided above a window that is provided on a top surface of the chamber and configured to pick up the image of the target inside the chamber through the window;
   an illuminator provided above the window and configured to irradiate light upwards;
   an illumination reflecting plate provided above the illuminator and including a reflecting surface configured to reflect the light from the illuminator towards the window; and a reflection restrictor directly attached to a surface that is the same as the reflecting surface of the illumination reflecting plate and configured to form a shadow in a predetermined region that includes the target inside the chamber.

2. The substrate position detecting apparatus as claimed in claim 1, wherein the illumination reflecting plate is provided below the imager, and includes an opening to secure a field of view of the imager with respect to the substrate.

3. The substrate position detecting apparatus as claimed in claim 1, wherein the reflection restrictor is located at a position to form the shadow in the predetermined region with reference to a region of the field of view of the imager.

4. The substrate position detecting apparatus as claimed in claim 1, wherein the target includes a first mark provided on a bottom surface of the chamber.

5. The substrate position detecting apparatus as claimed in claim 4, wherein the chamber includes a susceptor on which the substrate is set, and the target includes a second mark provided on a surface of the susceptor.

6. The substrate position detecting apparatus as claimed in claim 1, wherein the chamber includes a substrate holder configured to hold the substrate, and the target includes a boundary between the substrate holding part and the substrate.

7. The substrate position detecting apparatus as claimed in claim 6, wherein the substrate holding part includes a pick of a transport arm configured to transport the substrate into or out from the chamber.

8. The substrate position detecting apparatus as claimed in claim 5, wherein the susceptor is configured to hold a plurality of substrates, and the first mark is provided in correspondence with each of the plurality of substrates set on the susceptor.

9. The substrate position detecting apparatus as claimed in claim 5, wherein the susceptor is made of quartz, and the second mark is a colored mark.

10. The substrate position detecting apparatus as claimed in claim 1, wherein the chamber deposits a film on the substrate using a gas.

11. The substrate position detecting apparatus as claimed in claim 10, wherein the chamber deposits a colored film having reflectivity.

12. A substrate processing apparatus comprising:
the chamber including the top surface provided with the window, configured to process the substrate inside the chamber;
a susceptor on which the substrate is set, provided inside the chamber; and
the substrate position detecting apparatus as claimed in claim 5,
wherein the susceptor further includes a third mark formed by a cutout in a part of the susceptor, located in a vicinity of the second mark.

13. The substrate processing apparatus as claimed in claim 12, wherein the part of the susceptor where the cutout is formed is an edge part of the susceptor.

14. The substrate processing apparatus as claimed in claim 12, wherein the third mark has a cylindrical shape.

15. The substrate processing apparatus as claimed in claim 12, wherein the third mark has a tapered shape such that a size of the cutout increases from an upper surface of the susceptor towards a lower surface of the susceptor.

16. The substrate processing apparatus as claimed in claim 15, wherein a taper angle of the tapered shape is greater than an incident angle of the light from the illumination reflecting plate.

17. The substrate processing apparatus as claimed in claim 12, wherein the second mark and the third mark are selectively used, and further comprising:
a susceptor mark selecting switch configured to select the second mark or the third mark.

18. The substrate processing apparatus as claimed in claim 12, wherein the second mark and the third mark are selectively used, and further comprising:
a processor to judge whether to use the second mark or the third mark according to visibility of the second mark.

* * * * *